US010817760B2

(12) United States Patent
Pradeep et al.

(10) Patent No.: US 10,817,760 B2
(45) Date of Patent: Oct. 27, 2020

(54) ASSOCIATING SEMANTIC IDENTIFIERS WITH OBJECTS

(71) Applicant: Microsoft Technology Licensing, LLC, Redmond, WA (US)

(72) Inventors: Vivek Pradeep, Snohomish, WA (US); Michelle Lynn Holtmann, Kent, WA (US); Steven Nabil Bathiche, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 15/832,656

(22) Filed: Dec. 5, 2017

(65) Prior Publication Data

US 2018/0232608 A1 Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G06K 9/00* (2006.01)
*G06K 9/72* (2006.01)
(Continued)

(52) U.S. Cl.
CPC ............ *G06K 9/726* (2013.01); *A61B 5/0205* (2013.01); *A61B 5/0507* (2013.01); *A61B 5/117* (2013.01);
(Continued)

(58) Field of Classification Search
CPC ............... G06K 9/726; G06K 9/00973; G06K 9/00261; G06K 9/00295; G06K 9/00711;
(Continued)

(56) References Cited

U.S. PATENT DOCUMENTS 6,067,673 A   5/2000 Paese et al.
6,119,088 A   9/2000 Ciluffo
(Continued)

FOREIGN PATENT DOCUMENTS

EP   2947476 A1   11/2015
GB   2522922 A    8/2015
(Continued)

OTHER PUBLICATIONS

"SARA: the Socially Aware Robot Assistant", Retrieved from: https://web.archive.org/web/20160707141922/http:/articulab.hcii.cs.cmu.edu:80/projects/sara/, Jul. 7, 2017, 10 Pages.
(Continued)

*Primary Examiner* — Tom Y Lu

(74) *Attorney, Agent, or Firm* — Alleman Hall Creasman & Tuttle LLP

(57) ABSTRACT

Computing devices and methods for associating a semantic identifier with an object are disclosed. In one example, a three-dimensional model of an environment comprising the object is generated. Image data of the environment is sent to a user computing device for display by the user computing device. User input comprising position data of the object and the semantic identifier is received. The position data is mapped to a three-dimensional location in the three-dimensional model at which the object is located. Based at least on mapping the position data to the three-dimensional location of the object, the semantic identifier is associated with the object.

16 Claims, 9 Drawing Sheets

(51) Int. Cl.
| | |
|---|---|
| *G06T 7/70* | (2017.01) |
| *G06K 9/62* | (2006.01) |
| *G06F 3/16* | (2006.01) |
| *G10L 15/18* | (2013.01) |
| *G06N 20/00* | (2019.01) |
| *G06T 7/292* | (2017.01) |
| *H04W 4/33* | (2018.01) |
| *H04W 4/029* | (2018.01) |
| *A61B 5/11* | (2006.01) |
| *A61B 5/117* | (2016.01) |
| *A61B 5/00* | (2006.01) |
| *G01S 5/28* | (2006.01) |
| *G06F 1/3206* | (2019.01) |
| *G06F 1/3231* | (2019.01) |
| *G06F 1/324* | (2019.01) |
| *G06F 3/01* | (2006.01) |
| *G06F 3/03* | (2006.01) |
| *G06F 21/32* | (2013.01) |
| *G10L 17/04* | (2013.01) |
| *G10L 17/08* | (2013.01) |
| *H04L 12/58* | (2006.01) |
| *H04L 29/08* | (2006.01) |
| *H04N 5/232* | (2006.01) |
| *H04N 7/18* | (2006.01) |
| *H04N 21/422* | (2011.01) |
| *H04N 21/442* | (2011.01) |
| *G07C 9/28* | (2020.01) |
| *G06F 40/35* | (2020.01) |
| *G06F 40/211* | (2020.01) |
| *G06T 7/73* | (2017.01) |
| *G06T 7/246* | (2017.01) |
| *G01S 5/18* | (2006.01) |
| *G06T 7/60* | (2017.01) |
| *G10L 15/22* | (2006.01) |
| *G10L 15/28* | (2013.01) |
| *H04R 1/40* | (2006.01) |
| *H04R 3/00* | (2006.01) |
| *H04N 5/33* | (2006.01) |
| *G10L 15/02* | (2006.01) |
| *G06N 5/02* | (2006.01) |
| *G06N 5/04* | (2006.01) |
| *G10L 15/06* | (2013.01) |
| *G10L 15/24* | (2013.01) |
| *G10L 15/26* | (2006.01) |
| *G10L 15/19* | (2013.01) |
| *G10L 15/08* | (2006.01) |
| *G10L 15/32* | (2013.01) |
| *G10L 25/51* | (2013.01) |
| *H04L 29/06* | (2006.01) |
| *A61B 5/0205* | (2006.01) |
| *A61B 5/05* | (2006.01) |
| *G06F 21/35* | (2013.01) |
| *G08B 13/14* | (2006.01) |
| *G06F 3/0482* | (2013.01) |
| *G06F 3/0484* | (2013.01) |
| *H04N 21/231* | (2011.01) |
| *G06F 3/0488* | (2013.01) |
| *G06F 16/70* | (2019.01) |
| *G01S 11/14* | (2006.01) |
| *G01S 13/86* | (2006.01) |
| *G06N 3/04* | (2006.01) |
| *G08B 29/18* | (2006.01) |
| *G10L 17/00* | (2013.01) |
| *G07C 9/32* | (2020.01) |
| *H04N 5/247* | (2006.01) |
| *G01S 13/38* | (2006.01) |
| *G01S 13/88* | (2006.01) |

(52) U.S. Cl.
CPC ......... *A61B 5/1113* (2013.01); *A61B 5/7475* (2013.01); *G01S 5/18* (2013.01); *G01S 5/28* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 21/32* (2013.01); *G06F 21/35* (2013.01); *G06F 40/211* (2020.01); *G06F 40/35* (2020.01); *G06K 9/00* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/28* (2020.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/32* (2020.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L 2015/228* (2013.01); *H04N 5/247* (2013.01); *Y02D 10/126* (2018.01); *Y02D 10/173* (2018.01)

(58) Field of Classification Search
CPC .............. G06K 9/6255; G06K 9/6296; G06K 9/00288; G06K 9/00255; G06K 9/00342; G06K 9/00214; G06K 9/6289; G06K 9/6254; G06K 2209/09; H04W 4/00; H04L 67/22; H04L 51/02; H04L 63/102; G06N 20/00; G06N 5/047; G06N 5/025; G06N 3/0445; H04N 7/188; H04N 7/181; H04N 21/231; H04N 5/247; H04N 5/332; G06T 7/292; G06T 7/74; G06T 7/60; G06T 7/248; G06T 7/70; G06T 2207/10016; G06T 2207/10024; G06T 2207/30201; G06T 2207/30232; G06T 2207/30204; G06T 2207/20101; G10L 17/08; G10L 17/04; G10L 15/26; G10L 15/1822; G10L 15/063; G10L 25/51; G10L 15/24; G10L 15/28; G10L 15/18; G10L 15/22; G10L 15/19; G10L 15/08; G10L 15/02; G10L 15/32; G10L 2015/228; G10L 17/00; G10L 2015/223; G10L 2207/30196; G10L 2015/225; G10L 2015/088; G10L 2015/0635; G06F 21/32; G06F 3/0304; G06F 3/011; G06F 1/324; G06F 1/3231; G06F 1/3206; G06F 17/279; G06F 3/04842; G06F 3/017; G06F 21/35; G06F 17/271; G06F 3/0482; G06F 3/167; G06F 16/70; G06F 2203/0381; G06F 3/0488; G01S 5/28; G01S 13/726; G01S 5/18; G01S 13/867; G01S 11/14; G01S 5/16; G01S 13/888; G01S 13/38; G07C 9/00111; G07C 9/00134; H04R 1/406; H04R 3/005; G08B 13/1427; A61B 5/0507; A61B 5/0205; Y02D 10/173; Y02D 10/126

See application file for complete search history.

(56) References Cited

U.S. PATENT DOCUMENTS

| | | | |
|---|---|---|---|
| 6,332,122 B1 | 12/2001 | Ortega et al. | |
| 6,442,524 B1 | 8/2002 | Ecker et al. | |
| 6,477,500 B2 | 11/2002 | Maes | |
| 6,496,799 B1 | 12/2002 | Pickering | |
| 6,574,601 B1 | 6/2003 | Brown et al. | |
| 6,727,925 B1 * | 4/2004 | Bourdelais | G06T 19/00 715/850 |
| 6,728,679 B1 | 4/2004 | Strubbe et al. | |
| 6,816,730 B2 | 11/2004 | Davies et al. | |
| 6,873,953 B1 | 3/2005 | Lennig | |
| 7,019,749 B2 | 3/2006 | Guo et al. | |
| 7,050,110 B1 | 5/2006 | Lienhart et al. | |
| 7,330,566 B2 | 2/2008 | Cutler | |
| 7,475,010 B2 | 1/2009 | Chao | |
| 7,610,365 B1 | 10/2009 | Kraft et al. | |
| 7,716,056 B2 | 5/2010 | Weng et al. | |
| 7,803,050 B2 | 9/2010 | Mao et al. | |
| 8,139,945 B1 | 3/2012 | Amir et al. | |
| 8,165,087 B2 | 4/2012 | Panabaker | |
| 8,170,875 B2 | 5/2012 | Hetherington et al. | |
| 8,213,689 B2 | 7/2012 | Yagnik et al. | |
| 8,265,252 B2 | 9/2012 | Ducheneaut et al. | |
| 8,326,627 B2 | 12/2012 | Kennewick et al. | |
| 8,340,975 B1 | 12/2012 | Rosenberger | |
| 8,374,879 B2 | 2/2013 | Falcon et al. | |
| 8,453,402 B2 | 6/2013 | Huang | |
| 8,457,959 B2 | 6/2013 | Kaiser | |
| 8,543,402 B1 | 9/2013 | Ma | |
| 8,639,762 B2 | 1/2014 | Rasmussen et al. | |
| 8,644,842 B2 | 2/2014 | Arrasvuori et al. | |
| 8,712,758 B2 | 4/2014 | Crouch et al. | |
| 8,752,145 B1 | 6/2014 | Dotan et al. | |
| 8,762,150 B2 | 6/2014 | Edgington et al. | |
| 8,762,156 B2 | 6/2014 | Chen | |
| 8,779,965 B2 | 7/2014 | Sentelle et al. | |
| 8,805,691 B2 | 8/2014 | Genly | |
| 8,861,924 B2 | 10/2014 | Meads et al. | |
| 8,862,156 B2 | 10/2014 | Bell et al. | |
| 8,885,882 B1 | 11/2014 | Reale et al. | |
| 8,903,128 B2 | 12/2014 | Shet et al. | |
| 8,913,103 B1 | 12/2014 | Sargin et al. | |
| 8,942,986 B2 | 1/2015 | Cheyer et al. | |
| 8,949,359 B2 | 2/2015 | Rasmussen et al. | |
| 9,037,601 B2 | 5/2015 | Palay | |
| 9,070,366 B1 | 6/2015 | Mathias et al. | |
| 9,085,303 B2 | 7/2015 | Wolverton et al. | |
| 9,119,512 B2 | 9/2015 | Martins et al. | |
| 9,123,330 B1 | 9/2015 | Sharifi et al. | |
| 9,171,542 B2 | 10/2015 | Gandrabur et al. | |
| 9,230,544 B2 | 1/2016 | Kwon et al. | |
| 9,268,406 B2 | 2/2016 | Geisner et al. | |
| 9,300,925 B1 | 3/2016 | Zhang | |
| 9,307,355 B2 | 4/2016 | Nehrenz et al. | |
| 9,311,932 B2 | 4/2016 | Carter | |
| 9,318,105 B1 | 4/2016 | Khosla | |
| 9,348,990 B2 | 5/2016 | Chuaprasert et al. | |
| 9,368,114 B2 | 6/2016 | Larson et al. | |
| 9,378,740 B1 | 6/2016 | Rosen et al. | |
| 9,380,177 B1 | 6/2016 | Rao et al. | |
| 9,389,681 B2 | 7/2016 | Sankar et al. | |
| 9,412,392 B2 | 8/2016 | Lindahl | |
| 9,424,840 B1 | 8/2016 | Hart et al. | |
| 9,466,286 B1 | 10/2016 | Hart et al. | |
| 9,495,331 B2 | 11/2016 | Govrin et al. | |
| 9,495,613 B2 | 11/2016 | Holz et al. | |
| 9,507,977 B1 | 11/2016 | Mor et al. | |
| 9,508,341 B1 | 11/2016 | Parlikar et al. | |
| 9,514,227 B1 | 12/2016 | Garrett et al. | |
| 9,558,749 B1 | 1/2017 | Secker-Walker et al. | |
| 9,576,574 B2 | 2/2017 | van Os | |
| 9,622,059 B2 | 4/2017 | Bouzid et al. | |
| 9,626,352 B2 | 4/2017 | Allen et al. | |
| 9,633,652 B2 | 4/2017 | Kurniawati et al. | |
| 9,669,296 B1 * | 6/2017 | Hibbert | A63F 13/12 |
| 9,749,583 B1 | 8/2017 | Fineberg et al. | |
| 9,761,055 B2 * | 9/2017 | Miller | G06F 3/011 |
| 9,767,616 B2 * | 9/2017 | Miller | G06F 3/011 |
| 9,842,299 B2 | 12/2017 | Stolarz et al. | |
| 9,898,250 B1 | 2/2018 | Williams et al. | |
| 9,965,247 B2 | 5/2018 | Jarvis et al. | |
| 10,178,301 B1 | 1/2019 | Welbourne et al. | |
| 10,276,149 B1 | 4/2019 | Liang et al. | |
| 10,482,885 B1 | 11/2019 | Moniz | |
| 10,599,390 B1 | 3/2020 | Brahmbhatt et al. | |
| 2003/0103647 A1 | 6/2003 | Rui et al. | |
| 2003/0131064 A1 | 7/2003 | Bell et al. | |
| 2005/0182627 A1 | 8/2005 | Tanaka et al. | |
| 2005/0216264 A1 | 9/2005 | Attwater et al. | |
| 2005/0225427 A1 | 10/2005 | Bell et al. | |
| 2005/0285774 A1 | 12/2005 | Wittenberg et al. | |
| 2006/0028552 A1 | 2/2006 | Aggarwal et al. | |
| 2006/0067536 A1 | 3/2006 | Culbert et al. | |
| 2007/0024487 A1 | 2/2007 | Zemany et al. | |
| 2007/0100480 A1 | 5/2007 | Sinclair et al. | |
| 2007/0152157 A1 | 7/2007 | Page | |
| 2007/0198245 A1 | 8/2007 | Kamatani et al. | |
| 2007/0271086 A1 | 11/2007 | Peters et al. | |
| 2008/0030345 A1 | 2/2008 | Austin et al. | |
| 2008/0071547 A1 | 3/2008 | Prieto et al. | |
| 2008/0077015 A1 | 3/2008 | Boric-lubecke et al. | |
| 2008/0195387 A1 | 8/2008 | Zigel et al. | |
| 2008/0288251 A1 | 11/2008 | Cooper et al. | |
| 2009/0066690 A1 | 3/2009 | Harrison | |
| 2009/0303342 A1 | 12/2009 | Corcoran et al. | |
| 2009/0319269 A1 | 12/2009 | Aronowitz | |
| 2010/0073363 A1 * | 3/2010 | Densham | G05B 17/02 345/419 |
| 2010/0100851 A1 | 4/2010 | Clark et al. | |
| 2010/0179813 A1 | 7/2010 | Summerfield et al. | |
| 2010/0195906 A1 | 8/2010 | Uliyar et al. | |

(56) References Cited

U.S. PATENT DOCUMENTS

| | | |
|---|---|---|
| 2011/0010170 A1 | 1/2011 | Burns et al. |
| 2011/0119060 A1 | 5/2011 | Aronowitz |
| 2011/0184735 A1 | 7/2011 | Flaks et al. |
| 2011/0216090 A1* | 9/2011 | Woo .................. G06K 9/00 345/633 |
| 2011/0219339 A1* | 9/2011 | Densham ............. G06T 15/00 715/849 |
| 2011/0298967 A1 | 12/2011 | Clavin et al. |
| 2011/0302535 A1* | 12/2011 | Clerc .................. G06F 3/04815 715/848 |
| 2012/0026335 A1 | 2/2012 | Brown et al. |
| 2012/0253791 A1 | 10/2012 | Heck et al. |
| 2012/0265535 A1 | 10/2012 | Bryant-Rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0144616 A1 | 6/2013 | Bangalore |
| 2013/0212501 A1 | 8/2013 | Anderson et al. |
| 2013/0253936 A1 | 9/2013 | Harvey |
| 2013/0259456 A1 | 10/2013 | Viswanathan |
| 2013/0304479 A1 | 11/2013 | Teller et al. |
| 2013/0342568 A1 | 12/2013 | Ambrus et al. |
| 2014/0033071 A1 | 1/2014 | Gruber et al. |
| 2014/0067679 A1 | 3/2014 | O'reilly et al. |
| 2014/0100997 A1* | 4/2014 | Mayerle ............. G06Q 30/0643 705/27.2 |
| 2014/0156276 A1 | 6/2014 | Nakano et al. |
| 2014/0160290 A1 | 6/2014 | Wu |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0272821 A1 | 9/2014 | Pitschel et al. |
| 2014/0330569 A1 | 11/2014 | Kolavennu et al. |
| 2014/0341440 A1 | 11/2014 | Walch |
| 2014/0365226 A1 | 12/2014 | Sinha |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032254 A1 | 1/2015 | Ishiguro |
| 2015/0032456 A1 | 1/2015 | Wait |
| 2015/0035976 A1 | 2/2015 | Mayuzumi |
| 2015/0102996 A1 | 4/2015 | Yim et al. |
| 2015/0134547 A1* | 5/2015 | Oikonomidis ..... G06Q 30/0278 705/306 |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0195666 A1 | 7/2015 | Massey et al. |
| 2015/0220244 A1 | 8/2015 | Vats et al. |
| 2015/0249664 A1 | 9/2015 | Talhami et al. |
| 2015/0279368 A1 | 10/2015 | Contolini et al. |
| 2015/0340033 A1 | 11/2015 | Di fabbrizio et al. |
| 2015/0347114 A1 | 12/2015 | Yoon |
| 2015/0371639 A1 | 12/2015 | Foerster et al. |
| 2015/0382047 A1 | 12/2015 | Van os et al. |
| 2016/0019889 A1 | 1/2016 | Alvarez guevara et al. |
| 2016/0063989 A1 | 3/2016 | Deleeuw |
| 2016/0086018 A1 | 3/2016 | Lemoff |
| 2016/0088043 A1 | 3/2016 | Jiang et al. |
| 2016/0092732 A1 | 3/2016 | Black |
| 2016/0138247 A1 | 5/2016 | Conway et al. |
| 2016/0148417 A1 | 5/2016 | Kim et al. |
| 2016/0155443 A1 | 6/2016 | Khan et al. |
| 2016/0171289 A1 | 6/2016 | Lee et al. |
| 2016/0173293 A1 | 6/2016 | Kennedy |
| 2016/0179831 A1 | 6/2016 | Gruber et al. |
| 2016/0187961 A1 | 6/2016 | Elibol et al. |
| 2016/0203002 A1 | 7/2016 | Kannan et al. |
| 2016/0210411 A1 | 7/2016 | Mentis |
| 2016/0217783 A1 | 7/2016 | Konuma et al. |
| 2016/0225373 A1 | 8/2016 | Casado et al. |
| 2016/0234595 A1 | 8/2016 | Goran et al. |
| 2016/0234616 A1 | 8/2016 | Gateau |
| 2016/0259623 A1 | 9/2016 | Sumner et al. |
| 2016/0283185 A1 | 9/2016 | Mclaren et al. |
| 2016/0342702 A1 | 11/2016 | Barve et al. |
| 2016/0358598 A1 | 12/2016 | Williams et al. |
| 2016/0360336 A1 | 12/2016 | Gross et al. |
| 2016/0380929 A1 | 12/2016 | Katis et al. |
| 2017/0013409 A1 | 1/2017 | Cerchio et al. |
| 2017/0025124 A1 | 1/2017 | Mixter et al. |
| 2017/0032021 A1 | 2/2017 | Watanachote |
| 2017/0032787 A1 | 2/2017 | Dayal |
| 2017/0039423 A1 | 2/2017 | Cork et al. |
| 2017/0039602 A1 | 2/2017 | Shi-nash et al. |
| 2017/0068423 A1 | 3/2017 | Napolitano et al. |
| 2017/0078573 A1 | 3/2017 | Chen et al. |
| 2017/0133011 A1 | 5/2017 | Chen et al. |
| 2017/0140760 A1 | 5/2017 | Sachdev |
| 2017/0169476 A1 | 6/2017 | Nomula et al. |
| 2017/0185375 A1 | 6/2017 | Martel et al. |
| 2017/0186290 A1 | 6/2017 | Li et al. |
| 2017/0194000 A1 | 7/2017 | Itani et al. |
| 2017/0206900 A1 | 7/2017 | Lee et al. |
| 2017/0230705 A1 | 8/2017 | Pardue et al. |
| 2017/0236512 A1 | 8/2017 | Williams et al. |
| 2017/0242651 A1 | 8/2017 | Lang et al. |
| 2017/0249309 A1 | 8/2017 | Sarikaya |
| 2017/0255450 A1* | 9/2017 | Mullins .................. G06F 8/315 |
| 2017/0262472 A1 | 9/2017 | Goldenberg |
| 2017/0269975 A1 | 9/2017 | Wood et al. |
| 2017/0278480 A1 | 9/2017 | Sung et al. |
| 2017/0286530 A1 | 10/2017 | Paruchuri et al. |
| 2017/0287490 A1 | 10/2017 | Biswal et al. |
| 2017/0315208 A1 | 11/2017 | Sadr |
| 2017/0322939 A1 | 11/2017 | Byron et al. |
| 2017/0351749 A1 | 12/2017 | Quirk et al. |
| 2017/0357637 A1 | 12/2017 | Nell et al. |
| 2017/0359666 A1 | 12/2017 | Lyren et al. |
| 2018/0009118 A1 | 1/2018 | Yamaga et al. |
| 2018/0047394 A1 | 2/2018 | Tian et al. |
| 2018/0048768 A1 | 2/2018 | Spittle et al. |
| 2018/0074785 A1 | 3/2018 | Ohmura |
| 2018/0090143 A1 | 3/2018 | Saddler et al. |
| 2018/0091782 A1 | 3/2018 | Bashkin |
| 2018/0096696 A1 | 4/2018 | Mixter |
| 2018/0158454 A1 | 6/2018 | Campbell et al. |
| 2018/0199123 A1 | 7/2018 | Rao et al. |
| 2018/0218080 A1 | 8/2018 | Krishnamurthy et al. |
| 2018/0231653 A1 | 8/2018 | Pradeep et al. |
| 2018/0232201 A1 | 8/2018 | Holtmann |
| 2018/0232563 A1 | 8/2018 | Albadawi et al. |
| 2018/0232571 A1 | 8/2018 | Bathiche et al. |
| 2018/0232645 A1 | 8/2018 | Finkelstein et al. |
| 2018/0232662 A1 | 8/2018 | Solomon et al. |
| 2018/0232902 A1 | 8/2018 | Albadawi et al. |
| 2018/0233132 A1 | 8/2018 | Herold et al. |
| 2018/0233139 A1 | 8/2018 | Finkelstein et al. |
| 2018/0233140 A1 | 8/2018 | Koishida et al. |
| 2018/0233141 A1 | 8/2018 | Solomon et al. |
| 2018/0233142 A1 | 8/2018 | Koishida et al. |
| 2018/0233145 A1 | 8/2018 | Bathiche et al. |
| 2018/0260680 A1 | 9/2018 | Finkelstein et al. |
| 2018/0293221 A1 | 10/2018 | Finkelstein et al. |
| 2018/0314689 A1 | 11/2018 | Wang et al. |
| 2018/0333862 A1 | 11/2018 | Hayashi |
| 2019/0057703 A1 | 2/2019 | Zeinstra |
| 2020/0012906 A1 | 1/2020 | Albadawi et al. |
| 2020/0042839 A1 | 2/2020 | Herold et al. |
| 2020/0104653 A1 | 4/2020 | Solomon et al. |

FOREIGN PATENT DOCUMENTS

| | | |
|---|---|---|
| KR | 1020070016280 A | 2/2007 |
| WO | 2007018523 A2 | 2/2007 |
| WO | 2010104772 A1 | 9/2010 |
| WO | 2013061268 A2 | 5/2013 |
| WO | 2015012449 A1 | 1/2015 |

(56) References Cited

FOREIGN PATENT DOCUMENTS

| WO | 2016114922 A1 | 7/2016 |
|---|---|---|
| WO | 2016162678 A1 | 10/2016 |
| WO | 2016205419 A1 | 12/2016 |

OTHER PUBLICATIONS

Arsikere, et al., "Computationally-efficient Endpointing Features for Natural Spoken Interaction with Personal-Assistant Systems", in Proceedings of IEEE International Conference on Acoustics, Speech and Signal Processing, May 4, 2014, pp. 3241-3245.

Ferrer, et al., "Is the Speaker Done Yet? Faster and More Accurate End-of-Utterance Detection using Prosody", in the proceedings of Seventh International Conference on Spoken Language Processing, Sep. 16, 2002, pp. 2061-2064.

Lacharite, Noelle, "Updated: Alexa Skills Kit Fact Template: Step-by-Step Guide to Build a Fact Skill", Retrieved from: https://developer.amazon.corniblogs/post/Tx3DVGG0K0TPUGQ/New-Alexa-Skills-Kit-Template:-Step-by-Step-Guide-to-Build-a-Fact-Skill, Mar. 29, 2016, 33 Pages.

"International Search Report and Written Opinion Issued in PCT Application No. PCT/US2018/017140", dated May 18, 2018, 12 Pages.

"International Search Report and Written Opinion Issued in PCT Application No. PCT/US2018/017514", dated May 17, 2018, 12 Pages.

Porcheron, et al., "Do Animals Have Accents?": Talking with Agents in Multi-Party Conversation, in Proceedings of 20th ACM Conference on Computer-Supported cooperative Work and Social Computing, Feb. 25, 2017, 14 Pages.

Xiang, Li, "Improving Knowledge Base Population With Information Extraction", a Thesis Submitted in Partial fulfillment of the Requirements of the University of New York for the Degree of Doctor of Philosophy, May 2016, 131 Pages.

Yun-Nung, Chen, "Unsupervised Learning and Modeling of Knowledge and Intent for Spoken Dialogue Systems", in Proceedings of the 53rd Annual Meeting of the Association for Computational Linguistics, Jul. 28, 2015, 8 Pages.

Zhang, et al., "A Joint Model of Intent Determination and Slot Filling for Spoken Language Understanding", in Proceedings of the Twenty-Fifth International Joint Conference on Artificial Intelligence, Jul. 9, 2016, pp. 2993-2999.

Panzarino, Matthew, "Here's an Actual 3D Indoor Map of a Room Captured With Google's Project Tango Phone", Retrieved From <<https://techcrunch.com/2014102/21/heres-an-actual-3d-indoor-map-of-a-room-captured-with-googles-project-tango-phone/>>, Feb. 21, 2014, 6 Pages.

Staff, Appleinsider, "Amazon Alexa's 'Follow-Up Mode' Enables Successive Requests Without Trigger Word", Retrieved From https://appleinsider.com/articles/18/03/09/amazon-alexas-follow-up-mode-enables-successive-requests-without-trigger-word, Mar. 9, 2018, 7 Pages.

"Multiple Agents (Each Trained for Different Domain) for One Chat Bot?", Retrieved From https://discuss.api.ai/t/multiple-agents-each-trained-for-different-domain-for-one-chat-bot/1002, Jul. 1, 2016, 1 Page.

"Train the Natural Language Processing Classifiers", Retrieved From https://www.mindmeld.com/docs/train_the_natural_language_processing_classifiers.html, Retrieved on: May 2, 2017, 10 Pages.

"Using Multiple Alexa Devices", Retrieved From https://www.amazon.com/gp/help/customer/display.html?nodeId=202013740, Apr. 24, 2017, 2 Pages.

"Application Filed in U.S. Appl. No. 15/395,961", filed Dec. 30, 2016, 79 Pages.

Ballan, et al., "Event Detection and Recognition for Semantic Annotation of Video", in Journal of Multimedia Tools and Applications, vol. 51, Issue 1, Nov. 10, 2010, pp. 279-302.

Beltagy, et al., "Improved Semantic Parsers for If-Then Statements", in Proceedings of the 54th Annual Meeting of the Association for Computational Linguistics, vol. 1, Aug. 7, 2016, pp. 726-736.

Boakye, et al., "Overlapped Speech Detection for Improved Speaker Diarization in Multiparty Meetings", in Proceedings of IEEE International Conference on Acoustics, Speech and Signal Processing, Mar. 31, 2008, 4 Pages.

Cho, et al., "A Multi-Sensor Fusion System for Moving Object Detection and Tracking in Urban Driving Environments", in IEEE International Conference on Robotics & Automation, May 31, 2014, 8 Pages.

Fossard, et al., "Between Anaphora and Deixis . . . the Resolution of the Demonstrative Noun Phrase that N", in Journal of Language and Cognitive Processes, vol. 27, Issue 9, Nov. 2, 2011, 3 Pages.

Gebhart, Andrew, "How to bring Alexa into every room of your home", Retrieved From https://www.cnet.com/how-to/how-to-install-alexa-in-every-room-of-your-home/, Feb. 2, 2017, 7 Pages.

Goncalves, et al., "Assessing Users' Emotion at Interaction Lime: A Multimodal Approach With Multiple Sensors", in Proceedings of Soft Computing, vol. 21, Issue 18, Sep. 1, 2017, 8 Pages.

Goswami, et al., "A Reviewon Low Light Image Enhancement Using Image Processing Technique", in International Journal of Technical Research, vol. 5, Issue 1, Mar. 2016, pp. 60-62.

He, et al., "Sensor Scheduling for Target Tracking: A Monte Carlo sampling approach", in Journal of Digital Signal Processing, vol. 16, Issue 5, Sep. 2006, pp. 533-545.

Huijbregts, et al., "Speech Overlap Detection in a Two-Pass Speaker Diarization System", in Proceedings of 10th Annual Conference of the International Speech Communication, Sep. 6, 2009, pp. 1063-1066.

Kabadjov, Mijail Alexandrov., "A Comprehensive Evaluation of Anaphora Resolution and Discourse-new Classification", in thesis of University of Essex, May 2007, 266 Pages.

Kang, et al., "Detection and Tracking of Moving Objects from Overlapping EO and IR Sensors", in Conference on Computer Vision and Pattern Recognition Workshop, Jun. 27, 2004, 6 Pages.

Kozhaya, Joe, "10 Steps to Train an Effective Chatbot and its Machine Learning Models", Retrieved From https://developer.ibm.com/dwblog/2016/10-steps-train-chat-bot-chatbot-machine-learning/, Dec. 12, 2016, 7 Pages.

Li, et al. "A Multiple-Camera System Calibration Toolbox Using a Feature Descriptor-based Calibration Pattern", in Proceedings of IEEE International Conference on Intelligent Robots and Systems, Nov. 3, 2013, pp. 1301-1307.

Liu, et al., "Reliable Multiple Object Tracking under Heavy Occlusions", in Proceedings on Intelligence Information Processing and Trusted Computing (IPTC), International Symposium, Oct. 28, 2010, 3 Pages.

Mengusoglu, Erhan, "Confidence Measures for Speech/Speaker Recognition and Applications on Turkish LVCSR", Retrieved From https://web.archive.org/web/20040619044603/http://www.tcts.fpms.ac.be/publications/phds/mengusoglu/thesis_mengus.pdf, Apr. 20, 2004, 143 Pages.

Verma et al., "Face Detection and Tracking in a Video by Propagating Detection Probabilities", in Proceedings of IEEE Transactions on Pattern Analysis and Machine Intelligence, vol. 25, Issue 10, Oct. 1, 2003, pp. 1215-1228.

M. K., et al., "Ambiguities in Natural Language Processing", in International Journal of Innovative Research in Computer and Communication Engineering, vol. 2, Special Issue 5, Oct. 2014, pp. 392-394.

Pan, et al., "Robust Occlusion Handling in Object Tracking", in IEEE Conference on Computer Vision and Pattern Recognition, Jun. 17, 2007, 8 Pages.

"International Search Report and Written Opinion Issued in PCT Application No. PCT/US18/017139", dated May 8, 2018, 13 Pages.

"International Search Report and Written Opinion Issued in PCT Application No. PCT/US2018/017506", dated May 4, 2018, 13 Pages.

"International Search Report and Written Opinion Issued in PCT Application No. PCT/US2018/017508", dated May 8, 2018, 13 Pages.

(56) References Cited

OTHER PUBLICATIONS

"International Search Report and Written Opinion Issued in PCT Application No. PCT/US2018/017509", dated May 11, 2018, 11 Pages.
"International Search Report and Written Opinion Issued in PCT Application No. PCT/US2018/017510", dated Apr. 20, 2018, 14 Pages.
"International Search Report and Written Opinion Issued in PCT Application No. PCT/US2018/017511", dated May 17, 2018, 12 Pages.
"International Search Report and Written Opinion Issued in PCT Application No. PCT/US2018/017512", dated May 4, 2018, 15 Pages.
"International Search Report and Written Opinion Issued in PCT Application No. PCT/US2018/017513", dated Apr. 12, 2018, 15 Pages.
"International Search Report and Written Opinion Issued in PCT Application No. PCT/US2018/017515", dated May 9, 2018, 12 Pages.
"International Search Report and Written Opinion Issued in PCT Application No. PCT/US2018/017517", dated May 11, 2018, 12 Pages.
Pullen, John Patrick., "Amazon Echo Tip: How to Add Multiple Users ! Time", Retrieved From http://time.com/4668359/amazon-echo-alexa-multiple-accounts/, Feb. 13, 2017, 3 Pages.
Quirk, et al., "Language to Code: Learning Semantic Parsers for If-This-Then-That Recipes", in Proceedings of the 53rd Annual Meeting of the Association for Computational Linguistics, Jul. 26, 2015, pp. 878-888.
Rizwan, et al., "Local Enhancement for Robust Face Detection in Poor SNR Images", in International Journal of Computer Science and Network Security, vol. 9, Issue 6, Jun. 2009, pp. 93-96.
Sinha, et al., "An Analysis Engine for Dependable Elicitation on Natural Language Use Case Description and its Application to Industrial Use Cases", in IBM Research Report, RC242712, Dec. 18, 2008, 12 Pages.
Toutanova, et al., "Compositional Learning of Embeddings for Relation Paths in Knowledge Bases and Text", in Proceedings of the 54th Annual Meeting of the Association for Computational Linguistics, Aug. 7, 2016, pp. 1434-1444.
Wagner, Martin, "Tracking with Multiple Sensors", Faculty of Computer Science at the Technical University of Munich, Sep. 12, 2004, 202 Pages.
Wheeler, et al., "Face Recognition at a Distance", in Publication of Springer, Jan. 2011, pp. 353-381.
Yamamoto, S, et al., "Algorithm Optimizations for Low-Complexity Eye Tracking", in Proceedings of IEEE International Conference on Systems, Man, and Cybernetics, Oct. 2009, pp. 18-22.
Kalal, et al., "Face-TLD: Tracking-Learning-Detection Applied to Faces", in Proceedings of 17th IEEE International Conference on Image Processing, Sep. 26, 2010, pp. 3789-3792.
Zotkin, et al., "Joint Audio-Visual Tracking Using Particle Filters", in Eurasip Journal on Applied Signal Processing, vol. 2002, Issue 1, Jan. 2002, pp. 1154-1164.
Yu, et al., "Smart Meeting Systems: a Survey of State of the Art and Open Issues", in the Proceedings of ACM Computing Surveys, vol. 42, No. 2, Mar. 5, 2010, 20 Pages.
Miro, et al., "Speaker Diarization: A review of Recent Research", in the Proceedings of IEEE Transactions on Audio, Speech and Language Processing, vol. 20, Issue 2, Feb. 1, 2012, 15 Pages.
Moattar, et al., "A Review on Speaker Diarization Systems and Approaches", in the Publication of Speech Communication , vol. 54, Issue 10, Dec. 12, 2010, 39 Pages.
"International Search Report & Written Opinion for PCT Patent Application No. PCT/US2018/062384", dated Feb. 15, 2019, 12 Pages.

"Non Provisional Application Filed in U.S. Appl. No. 15/885,518", filed Jan. 31, 2018, 40 Pages.
"Non Final Office Action Issued in U.S. Appl. No. 15/636,422", dated Sep. 4, 2018, 11 Pages.
"Non Final Office Action Issued in U.S. Appl. No. 15/640,251", dated Oct. 15, 2018, 22 Pages.
"Non Final Office Action Issued in U.S. Appl. No. 15/646,871", dated Dec. 19, 2018, 22 Pages.
"Non Final Office Action Issued in U.S. Appl. No. 15/656,994", dated Jan. 22, 2019, 8 Pages.
"Non Final Office Action Issued in U.S. Appl. No. 15/657,031", dated Oct. 5, 2018, 16 Pages.
"Non-Final Office Action Issued in U.S. Appl. No. 15/657,822", dated Feb. 21, 2019, 25 Pages.
"Final Office Action Issued in U.S. Appl. No. 15/640,251", dated Apr. 2, 2019, 22 Pages.
"Final Office Action Issued in U.S. Appl. No. 15/646,871", dated Apr. 19, 2019, 22 Pages.
"Non Final Office Action Issued in U.S. Appl. No. 15/682,407", dated Jun. 26, 2019,15 Pages.
"Non Final Office Action Issued in U.S. Appl. No. 15/682,425", dated May 6, 2019,12 Pages.
"Final Office Action Issued in U.S. Appl. No. 15/646,871", dated Sep. 3, 2019, 23 Pages.
"Final Office Action Issued in U.S. Appl. No. 15/657,822", dated Aug. 22, 2019, 22 Pages.
Constine, Josh, "Instagram launches selfie filters, copying the last big Snapchat feature", Retreived from https://techcrunch.com/2017/05/16/instagram-face-filters/, May 16, 2017, 10 Pages.
"International Search Report and Written Opinion Issued in PCT Application No. PCT/US2019/029558", dated Jun. 28, 2019, 10 Pages.
"Non Final Office Action Issued in U.S. Appl. No. 15/640,251", dated Sep. 12, 2019, 21 Pages.
"International Search Report and Written Opinion Issued in PCT Application No. PCT/US2019/022836", dated Jun. 24, 2019, 15 Pages.
"Non Final Office Action Issued in U.S. Appl. No. 16/005,470", dated Feb. 24, 2020, 11 Pages.
"Non Final Office Action Issued in U.S. Appl. No. 15/657,822", dated Feb. 6, 2020, 25 Pages.
"Final Office Action Issued in U.S. Appl. No. 15/646,871", dated Jan. 21, 2020, 23 Pages.
"Final Office Action Issued in U.S. Appl. No. 15/640,251", dated Jan. 30, 2020, 21 Pages.
"Notice of Allowance Issued in U.S. Appl. No. 16/573,677", dated Nov. 6, 2019, 9 Pages.
"Office Action Issued in European Patent Application No. 18707800.1", dated Jun. 4, 2020, 4 Pages.
"Office Action Issued in European Patent Application No. 18708508.9", dated May 28, 2020, 6 Pages.
"Non Final Office Action Issued in U.S. Appl. No. 15/640,113", dated May 14, 2020, 13 Pages.
"Non Final Office Action Issued in U.S. Appl. No. 15/640,201", dated May 27, 2020, 11 Pages.
"Notice of Allowance Issued in U.S. Appl. No. 15/832,672", dated Jun. 2, 2020, 11 Pages.
"Non Final Office Action Issued in U.S. Appl. No. 15/936,076", dated Apr. 15, 2020, 23 Pages.
"Non Final Office Action Issued in U.S. Appl. No. 15/646,871", dated Jul. 1, 2020, 24 Pages.
"Final Office Action Issued in U.S. Appl. No. 15/657,822", dated Aug. 7, 2020, 22 Pages.
"Notice of Allowance Issued in U.S. Appl. No. 15/640,251", dated Jul. 31, 2020, 11 Pages.
"Final Office Action Issued in U.S. Appl. No. 16/005,470", dated Sep. 4, 2020, 15 Pages.

* cited by examiner

ASSOCIATING SEMANTIC IDENTIFIERS WITH OBJECTS

CROSS REFERENCE TO RELATED APPLICATIONS

This application claims priority to U.S. Provisional Patent Application Ser. No. 62/459,020 filed Feb. 14, 2017, and to U.S. Provisional Patent Application Ser. No. 62/482,165 filed Apr. 5, 2017, the entirety of which are hereby incorporated herein by reference for all purposes.

BACKGROUND

Interacting with computing systems via natural interactions, such as one or more of voice recognition, gesture recognition, intent recognition, etc., enables natural user interface experiences. Such natural user interface experiences can be augmented when computing systems have information regarding semantic identifiers of the objects in their environment.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Examples are disclosed that relate to computing devices and methods for associating a semantic identifier with an object. In one example, a method comprises generating a three-dimensional model of an environment comprising the object, sending image data of the environment to a user computing device for display by the user computing device, receiving user input comprising position data of the object and a semantic identifier, mapping the position data to a three-dimensional location in the three-dimensional model at which the object is located, and based at least on mapping the position data to the three-dimensional location of the object, associating the semantic identifier with the object.

DETAILED DESCRIPTION

Interacting with computing systems using natural interactions, such as one or more of voice recognition, gesture recognition, motion detection, gaze detection, intent recognition, brain activity assessment, etc., enables natural user interface experiences. Such natural user interface experiences can be augmented when a user provides semantic identifiers for objects in their environment. By utilizing such semantic identifiers, a computing system may better understand what objects a user may be referring to.

In some examples, however, computing systems may not provide a convenient or natural experience by which a user may semantically label objects in the environment for subsequent recognition by the computing system. Accordingly, examples are disclosed that relate to computing devices and methods for associating a semantic identifier with an object. In some examples, associating a semantic identifier with an object may be performed by various smart assistant devices, which may take the form of personal assistant devices, security devices, home automation devices, etc.

As will be described below, in some cases a method for associating a semantic identifier with an object may be implemented as part of a smart assistant device in the form of a base computing device that is communicatively coupled to a separate user computing device. In these examples, the base computing device may be configured to interpret and respond to user inputs comprising voice instructions and queries, gestures and other natural interactions, for example by answering questions or performing actions.

Figure 1:
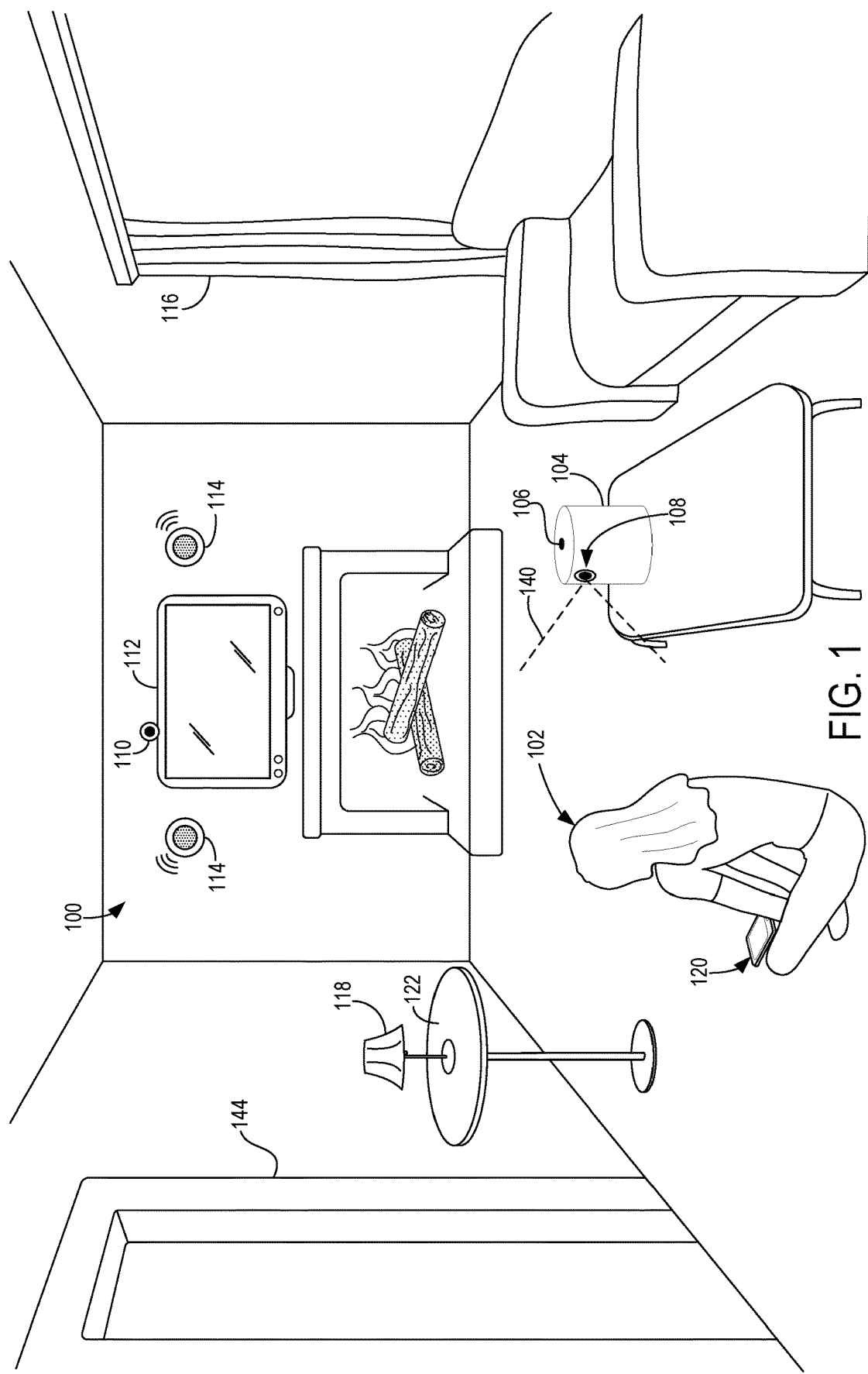
FIG. 1 is an illustrative example of a use case scenario in which a user operates a user computing device communicatively coupled to a base computing device according to examples of the present disclosure.

With reference now to FIG. 1, in one example a user 102 may be sitting in a living room 100 with a smart phone 120 and a smart assistant device in the form of base computing device 104. As described in more detail below, in some examples the user 102 may utilize smart phone 120 to help the user associate a semantic identifier with an object in the living room 100 via the base computing device 104.

The base computing device 104 may be configured to receive and process user inputs in the form of voice instructions and queries, gestures and other natural interactions. In this example, base computing device 104 comprises a microphone 106 and an image sensor 108, such as an RGB camera, IR sensor or other optical sensor. In some examples base computing device may comprise two or more microphones and/or two or more image sensors. In some examples, base computing device 104 may receive sensor data from one or more external sensors, such as an external camera 110. Base computing device 104 also may include one or more other types sensors.

User 102 may utilize the base computing device 104 for myriad functions. For example, the user 102 may provide natural language input to ask the base computing device 104 to perform a variety of tasks, such as provide information, change the state of another device, schedule a reminder, send a message, complete a purchase, etc. The base computing device 104 also may be utilized to receive and store messages and/or reminders to be delivered at an appropriate future time. Using data received from sensors, the base computing device 104 may track and/or communicate with one or more users or other entities.

In some examples, base computing device 104 may perform tasks programmatically without input from the user. For example, base computing device 104 may utilize sensor data, such as audio and/or video data, to detect when the user moves to another room and is looking at or engaged with another device. Using this data, base computing device 104 may automatically alter the state of the device accordingly. In some examples, the base computing device 104 also may be configured to control smart devices, appliances and other elements in the living room 100, such as a television 112, speakers 114 of a music system, motorized curtains 116, or lamp 118.

In some examples, the base computing device 104 may be operatively connected with one or more other computing devices using a wired connection, or may employ a wireless connection via Wi-Fi, Bluetooth, or any other suitable wireless communication protocol. For example, the base computing device 104 may be communicatively coupled to one or more other computing devices via a network. The network may take the form of a local area network (LAN), wide area network (WAN), wired network, wireless network, personal area network, or a combination thereof, and may include the Internet.

Figure 6:
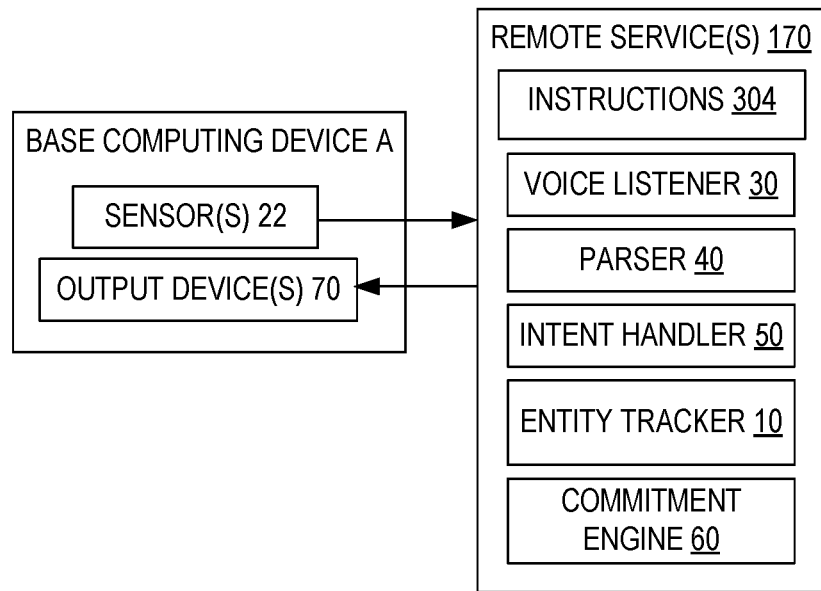
FIG. 6 schematically shows an example implementation in which one or more remote services perform aspects of associating a semantic identifier with an object according to examples of the present disclosure.
Figure 7:
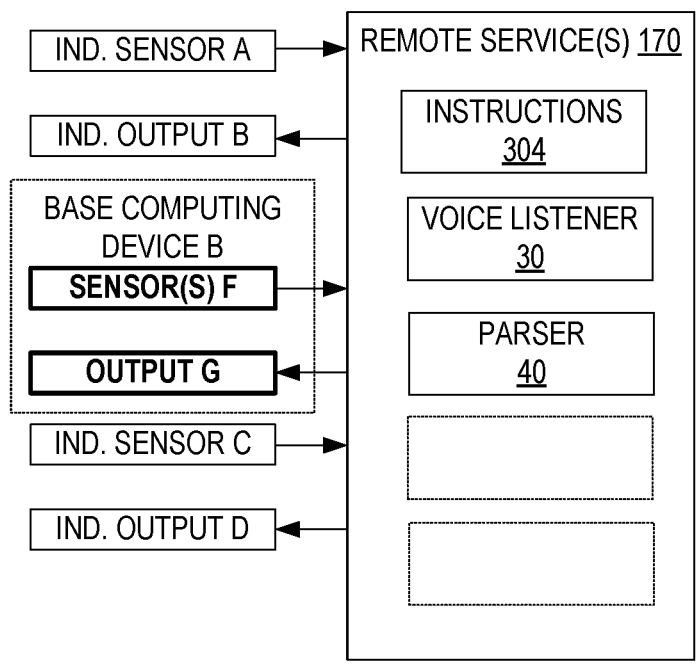
FIG. 7 schematically shows another example implementation in which one or more remote services perform aspects of associating a semantic identifier with an object according to examples of the present disclosure.

In the example of FIG. 1 and as described in more detail below, base computing device 104 is communicatively coupled via wireless network to smart phone 120. Additional details regarding components and computing aspects of the base computing device 104 are described in more detail below with reference to FIG. 10. It will be appreciated that the base computing device 104 of FIG. 1 is merely one example implementation of a smart assistant device for performing aspects of the present disclosure. Additional example implementations across two or more devices are illustrated in FIGS. 6 and 7 and described in more detail below.

Figure 2:
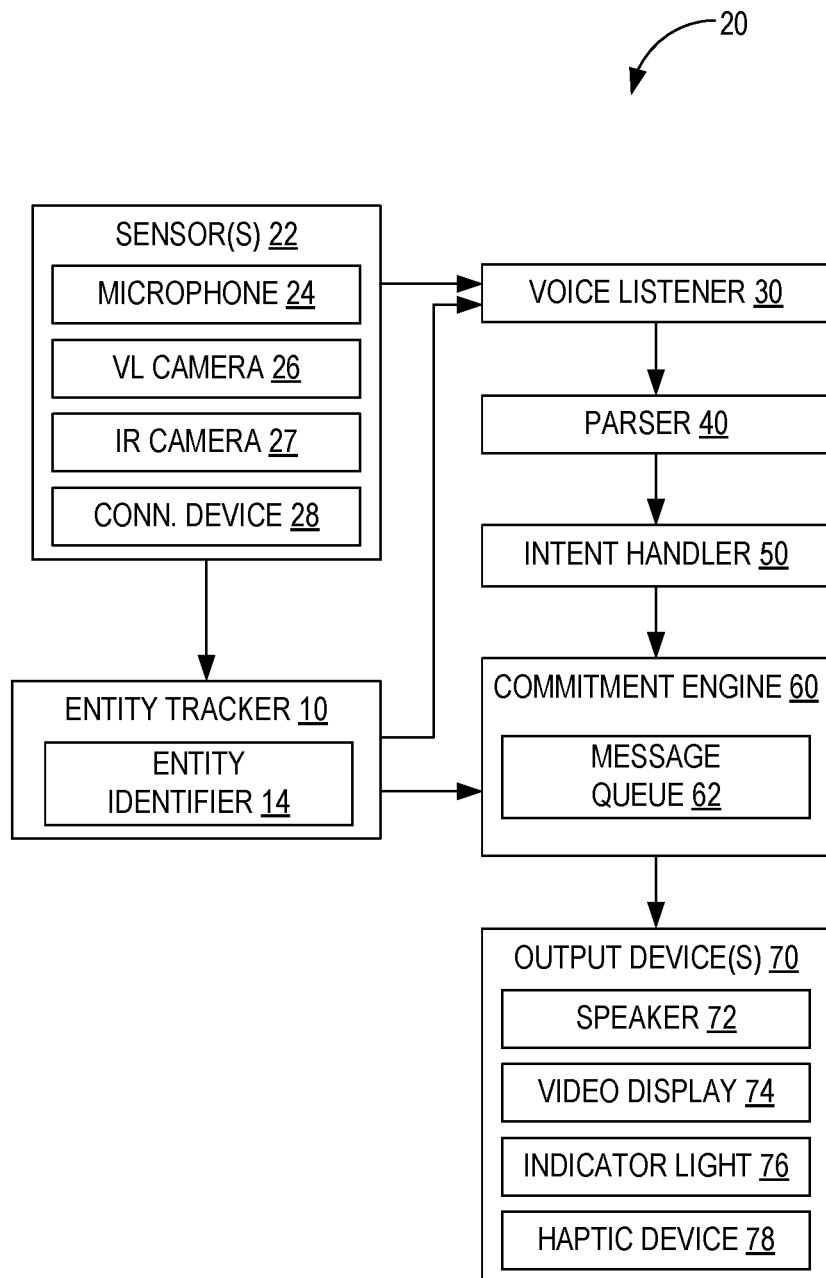
FIG. 2 schematically shows an example logical architecture for implementing a smart assistant computing system according to an example of the present disclosure.

FIG. 2 shows an example logical architecture for implementing a smart assistant system 20 capable of recognizing and responding to natural language inputs and associating a semantic identifier with an object, according to examples of the present disclosure. As described in more detail below, in various examples the system 20 may be implemented in a single all-in-one computing device, such as in base computing device 104, across two or more devices, in a cloud-supported network, and in combinations of the foregoing. In one example and with reference also to FIG. 4 described in more detail below, a base computing device may comprise one or more elements of the smart assistant system 20 for interpreting and responding to natural language inputs.

In the example of FIG. 2, the smart assistant system 20 includes at least one sensor 22, an entity tracker 10, a voice listener 30, a parser 40, an intent handler 50, a commitment engine 60, and at least one output device 70. In some examples the sensor(s) 22 may include one or more microphones 24, visible light (VL) cameras 26, infrared (IR) cameras 27, and connectivity devices 28, such as Wi-Fi or Bluetooth modules. In some examples sensor(s) 22 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 10 is configured to detect entities and their activities, including people, animals, or other living things, as well as non-living objects. Entity tracker 10 includes an entity identifier 14 that is configured to recognize individual users and/or non-living objects. Voice listener 30 receives audio data and utilizes speech recognition functionality to translate spoken utterances into text. Voice listener 30 also may assign confidence value(s) to the translated text, and may perform speaker recognition to determine an identity of the person speaking, as well as assign probabilities to the accuracy of such identifications. Parser 40 analyzes text and confidence values received from voice listener 30 to derive user intentions and generate corresponding machine-executable language.

Intent handler 50 receives machine-executable language representing user intentions from the parser 40, and resolves missing and ambiguous information to generate commitments. Commitment engine 60 stores commitments from the intent handler 50. At a contextually appropriate time, the commitment engine may deliver one or more messages and/or execute one or more actions that are associated with one or more commitments. Commitment engine 60 may store messages in a message queue 62 or cause one or more output devices 70 to generate output. The output devices 70 may comprise one or more of speaker(s) 72, video display(s) 74, indicator light(s) 76, haptic device(s) 78, and/or other suitable output devices. In other examples, output devices 70 may comprise one or more other devices or systems, such as home lighting, thermostats, media programs, door locks, etc., that may be controlled via actions executed by the commitment engine 60.

In different examples the voice listener 30, parser 40, intent handler 50, commitment engine 60, and/or entity tracker 10 may be embodied in software that is stored in memory and executed by one or more processors of a computing device. In some implementations, specially programmed logic processors may be utilized to increase the computational efficiency and/or effectiveness of the smart assistant device. Additional details regarding the components and computing aspects of computing devices that may store and execute these modules are described in more detail below with reference to FIG. 10.

In some examples, the voice listener 30 and/or commitment engine 60 may receive context information including associated confidence values from entity tracker 10. Entity tracker 10 may determine an identity, position, and/or current status of one or more entities within range of one or more sensors, and may output such information to one or more other modules, such as voice listener 30, commitment engine 60, etc. In some examples, entity tracker 10 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

In some examples, voice listener 30 may receive audio data from the surrounding environment. In some examples, such as in base computing device 104 of FIG. 1, the voice listener 30 may comprise a software module that is embodied in a standalone device that comprises one or more microphones. In other examples, the voice listener 30 software module may be stored in memory of a computing device that is located remotely from the user's environment, such as in a cloud-based service. In some examples, additional data from one or more other sensors may be received and utilized by the voice listener 30 in performing its functions that are described in more detail below.

Figure 3:
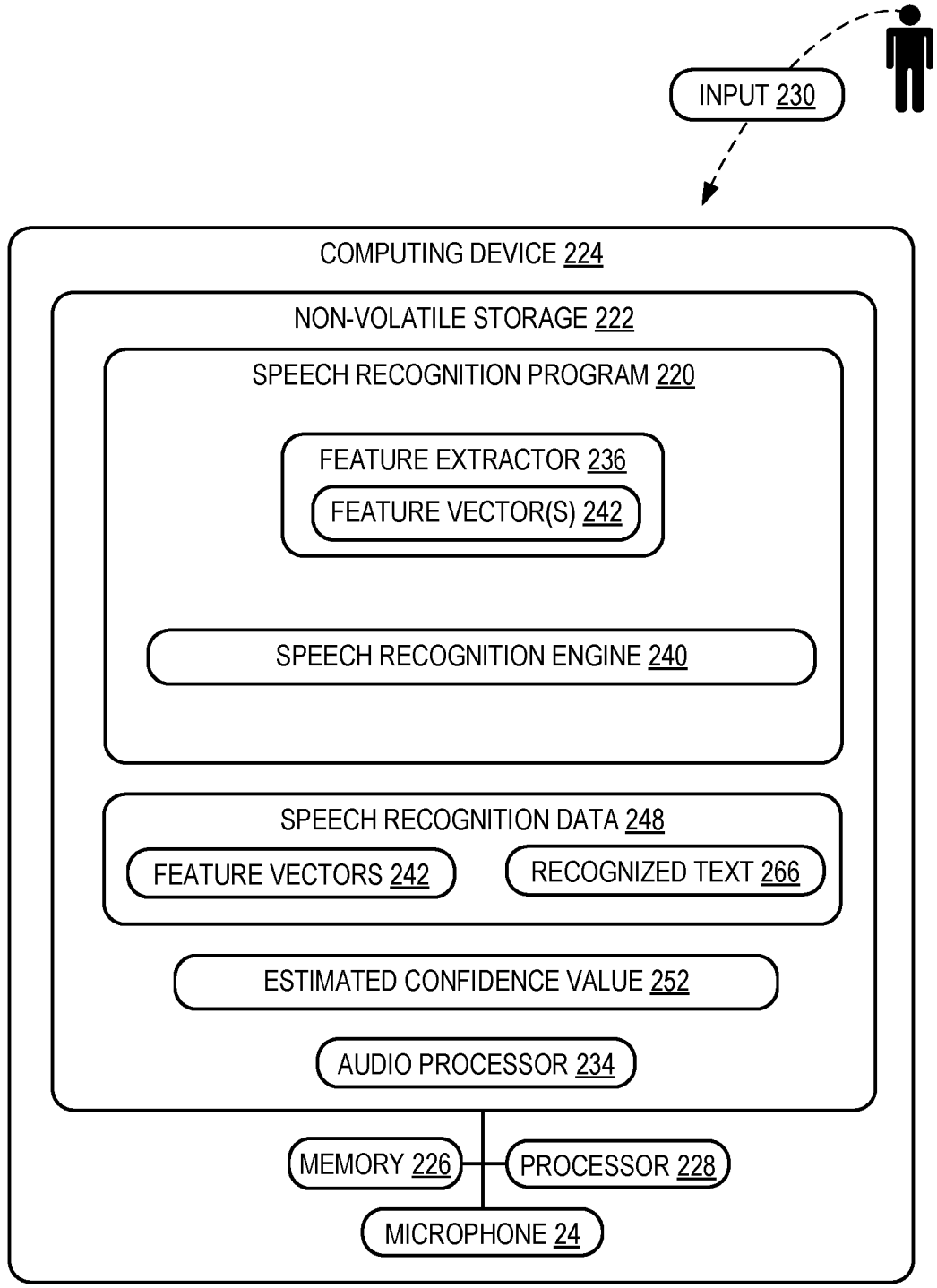
FIG. 3 schematically shows a speech recognition program that may be utilized by a voice listener according to an example of the present disclosure.

With reference now to FIG. 3, in some examples the voice listener 30 may comprise a speech recognition program 220 stored in non-volatile storage 222 of a computing device 224. The speech recognition program 220 may be loaded into memory 226 and executed by a processor 228 of computing device 224 to perform one or more of the methods and processes for speech recognition described in more detail below.

Audio input 230 in the form of natural language speech may be captured by microphone 24 and processed by audio processor 234 to create audio data. Audio data from the audio processor 234 may be transformed by feature extractor 236 into data for processing by a speech recognition engine 240 of the speech recognition program 220. Feature extractor 236 may utilize any suitable dimensionality reduction techniques to process the audio data and generate feature vectors 242. Example techniques include using mel-frequency cepstral coefficients (MFCCs), linear discriminant analysis, deep neural network techniques, etc.

Using the feature extractor 236 and speech recognition engine 240, the speech recognition program 220 may process feature vectors 242 and other speech recognition data 248 to generate recognized text 266. In other examples, any suitable techniques for matching feature vectors 242 to phonemes and/or other speech components may be utilized.

In some examples, the speech recognition program 220 may determine estimated confidence values 252 for one or more portions of the speech recognition data 248, such as individual speech components, words and phrases. An estimated confidence value 252 may define a statistical likelihood that the corresponding recognized text is accurate. The parser 40 of intelligent assistant system 20 may utilize such confidence values 252 in processing recognized text and determining a user's intent.

In different examples, confidence values 252 may be determined by utilizing one or more statistical analysis methods, machine learning techniques, empirically-derived data, and combinations of the foregoing. In some examples, the speech recognition program 220 may utilize one or more probabilistic models to analyze portions of the speech recognition data 248, one or more results extracted from the speech recognition analysis pipeline, and/or estimated confidence values 252 associated with such portions. For example, Gaussian Mixture Models (GMMs) may be utilized to analyze portions of the speech recognition data 248 and corresponding results. It will be appreciated that any other suitable machine learning techniques, such as various supervised learning and unsupervised learning approaches, may be utilized to analyze the speech recognition data 248.

It will be appreciated that the foregoing descriptions of speech recognition techniques are merely examples, and that any suitable speech recognition technologies and processes may be utilized and are contemplated within the scope of the present disclosure.

As indicated above, natural user interface experiences may be augmented when a user provides semantic identifiers for objects in their environment. In some examples, however, computing systems may not provide a convenient or natural method by which a user may semantically label objects in the environment for subsequent recognition by the computing system.

Figure 4:
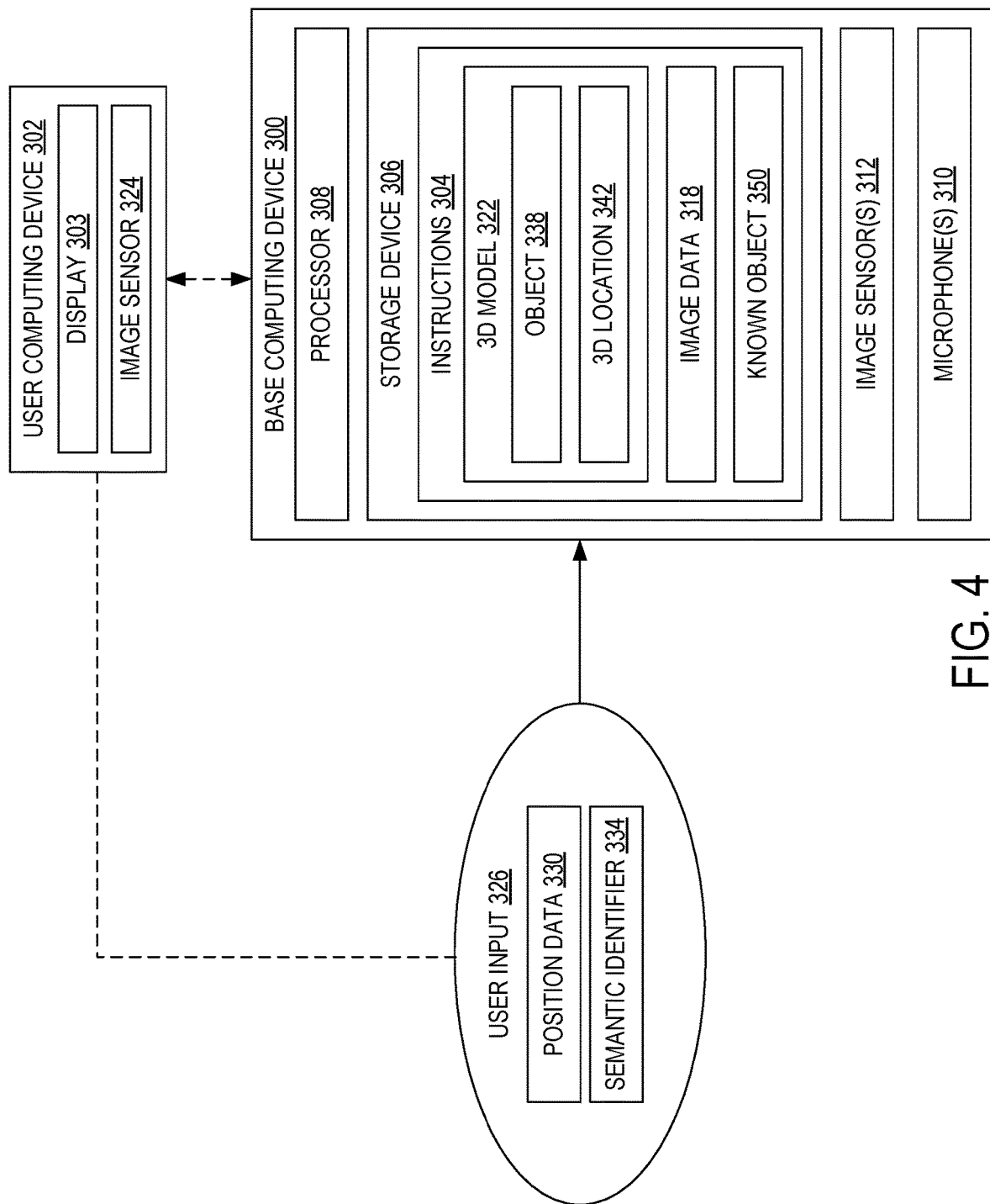
FIG. 4 shows a block diagram illustrating an example system for associating a semantic identifier with an object according to examples of the present disclosure.

Accordingly and with reference now to FIG. 4, an example system for associating a semantic identifier with an object will now be described. FIG. 4 illustrates a base computing device 300 which may take the form of base computing device 104 shown in FIG. 1. As noted above, base computing device 300 may be communicatively coupled to a user computing device 302, such as via a wired or wireless connection. In various examples the user computing device 302 may take the form of a smart phone, tablet or laptop computer, head-mounted display device, or other computing device that includes a display 303.

The base computing device 300 comprises instructions 304 that may be stored in storage device 306, loaded into memory and executed by a processor 308 to perform one or more of the methods and processes described herein. In other examples, one or more aspects of the methods and processes described herein may be performed remotely from the base computing device 300, such as in a cloud-based service. Base computing device 300 also may comprise one or more aspects of smart assistant system 20 described above. Additional details regarding the components and computing aspects of the base computing device 300 are described in more detail below with reference to FIG. 10.

Base computing device 300 comprises one or more microphones 310 and one or more image sensors 312 that may be utilized to capture image data 318. As described in more detail below, such image data 318 may be utilized to generate a three-dimensional (3D) model 322 of a physical environment. In different examples, image sensors 312 may comprise RGB cameras, IR sensors and/or other optical sensors. Image sensors 312 may capture image data 318 in the form of color, IR or other light information from the physical environment surrounding the sensors.

In some examples, such image data 318 may be used by the processor 308 to detect movements within a field of view of the base computing device 300, such as movements of objects, gesture-based inputs or other movements performed by a person (e.g., a pinching of fingers, closing of a fist, pointing with a finger or hand, etc.) that indicate an action to be taken or other user input. In some examples, such image data 318 may be used to determine that a user indicates or touches an object or other surface.

In some examples, base computing device 300 may include a depth sensor system that generates depth image data. The depth sensor system may include image sensors 312 in the form of one or more depth cameras that capture image data 318 from the physical environment. In some examples the depth camera(s) may be an infrared time-of-flight depth camera. In other examples the depth camera(s) may take the form of a structured light depth camera.

In some examples, the image sensors 312 may comprise two cameras in known positions functioning as a stereo pair to capture depth information. For example, the first image sensor may provide a first image and the second image sensor may provide a second image. A first pixel selected in the first image may be identified as corresponding to the same pixel in the second image to provide depth information about the selected pixel.

In some examples, image data captured by an image sensor 324 of the user computing device 302 also may be used to generate depth information of the surrounding environment. For example, the image sensor 312 of the base computing device 300 may have a sufficiently large field of view to overlap with the field of view of the image sensor 324 of the user computing device 302. In this manner, the base computing device 300 and the user computing device 302 may function as a stereo pair to obtain depth information from the image data 318 and image data captured by the user computing device, such as via triangulation techniques.

In some examples, image data from a single camera may be used to generate three-dimensional spatial information using a structure-from-motion technique. In one example, a user holding user computing device 302 may walk around a room while the image sensor 324 of user computing device 302 collects image data of the environment. Structure-from-motion techniques may be applied to the image data to obtain depth information.

Such techniques may include obtaining two images at two different positions within the environment to assemble temporal stereo image data. The two images may then be used as two images from a stereo pair of cameras, as previously discussed, to build a 3D model of the environment. In another example, the base computing device 300 may be moved around the room so that image sensor(s) 312 capture image data 318 of the environment to generate the 3D model of the environment 310.

In some examples, depth information obtained from the image data 318 and/or image data captured by user computing device 302 may be used to construct the 3D model 322 of the environment. In some examples, the 3D model 322 may comprise a surface mesh of the environment constructed using depth information obtained from the image data 318. In other examples, the 3D model 322 of the environment may not include a surface mesh.

In some examples, an object recognition system comprising an image classifier may be used to construct the 3D model 322 of the environment. The image classifier may outline one or more objects 338 in the image. In some examples, a user may outline an object 338 via user input to the user computing device 302, such as by drawing an outline of the object using a stylus. The object recognition system may then infer a 3D surface mesh on the object 338.

In some examples, the object classifier may infer a 3D surface mesh on an object 338 by partially or completely identifying the model or product family of the object. For example, a neural network may be trained on thousands of images of chairs, and therefore may be able to select a more specific wireframe of a particular model of chair by image classification. An object 338 that is fully recognized by the object recognition system may be segmented out of the image data 318 to generate 3D model 322.

In the examples described above, the object classifier, neural network, or other techniques used to generate the 3D model 322 of an environment may be maintained on any suitable device, such as the base computing device 300, or on another networked device such as a cloud service.

Returning to the example of FIG. 1, in some examples the user 102 may desire to semantically label one or more objects in her living room 100. As noted above, semantically labeling an object may provide more natural interaction with the base computing device 104 regarding the object. For example, using semantic identifiers may enable the base computing device 104 to better understand the user's intent underlying commands and requests made to the device.

In some examples and with reference again to FIG. 4, a user may semantically identify an object by providing user input 326 comprising position data 330 associated with the object from the user computing device 302 and a semantic identifier 334 to the base computing device 300. For example and as described in more detail below, a user may provide position data 330 of an object 338 in the environment while contemporaneously providing a semantic identifier 334 for the object. The base computing device 300 may then map the position data 330 to a 3D location 342 in the 3D model 322 at which the object 388 is located. Using the 3D location 342 of the object 388, the base computing device 300 may then associate the semantic identifier with the object, such as in metadata stored with an object identifier of the object.

In one example and with reference to FIG. 1, the user 102 may be going on vacation and would like the base computing device 104 to turn lamp 118 on and off at particular times while she's away. The user 102 may speak to the base computing device 104 and provide a command: "Hey computer, for the next week turn on the living room lamp at 5:00 pm and turn it off at 5:00 am." In this example, the user may want to semantically identify the lamp 118 as "the living room lamp."

In some examples, the user 102 may provide a command to the base computing device 104 to set a reminder and/or take an action with respect to an object or other entity that may not be otherwise identifiable, such as via a network address, part or model number, etc. For example, the user 102 may speak to the base computing device 104 and provide a command: "Hey computer, alert me if my son goes near the stove." In this example, the user may want to semantically identify the gas stove in the user's kitchen as "the stove."

In some examples, however, objects may be out of the field of view 140 of the base computing device 104, or the user 102 may be unsure whether an object is within the device's field of view. For example, the user 102 may be unsure if the lamp 118 is within the field of view 140 of the base computing device 104. In other examples, user 102 or another object may be blocking or partially occluding the base computing device 104 from viewing an object that otherwise would be in its field of view 140.

Accordingly, to help user 102 know that a desired object is in the field of view of the base computing device 104, the base computing device may send image data captured by image sensor 108 to the smart phone 120 for display by the phone. In this manner, the smart phone 120 may display the visual perspective of the base computing device 104 to confirm that the base computing device can see an object of interest, such as the lamp 118.

In some examples, the image data 318 sent to smart phone 120 may comprise a real-time video stream of the environment captured by the image sensor 108 of the base computing device 104. In this manner, the user 102 may see the real-time view of the base computing device 104. Accordingly, the user 102 may easily confirm whether an object of interest is within the field of view 140 of the base computing device 104. For example and with reference now to FIG. 5, the display 303 of the user's smart phone 120 may display a real-time video feed from the base computing device 104 that shows the lamp 188, table 122 and doorway 144 as viewed by the base computing device.

Figure 5:
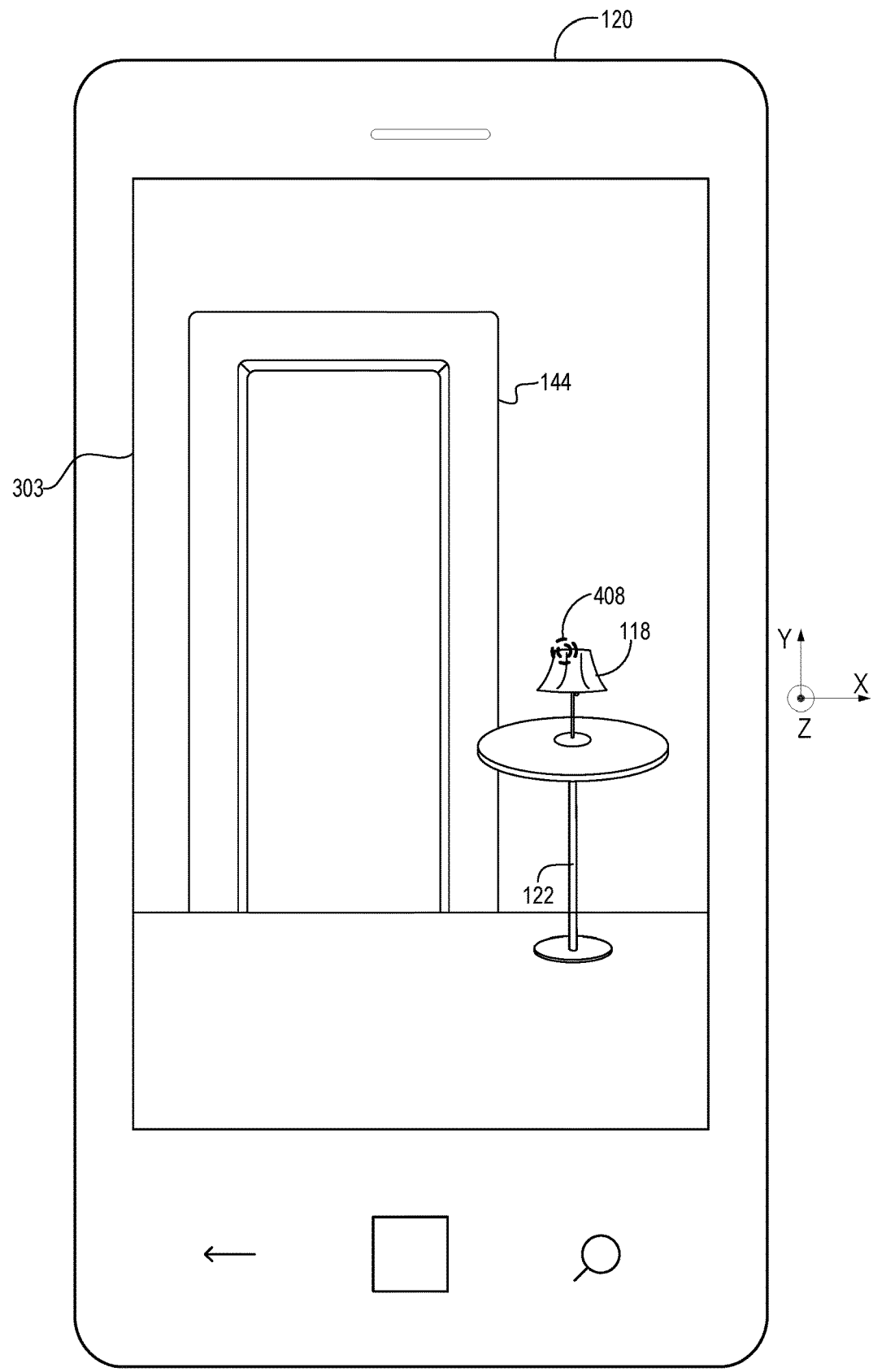
FIG. 5 shows the display of the user computing device of FIG. 1 according to an example of the present disclosure.

In some examples, the image data 318 displayed on the smart phone 120 may comprise a still image captured by the image sensor 108 of the base computing device 104. In some examples, the still image may be provided to the smart phone 120 via text message, email or other electronic delivery format. In other examples, the image data 318 displayed on the smart phone 120 may comprise a rendered image of the 3D model 322 of the room 100 as viewed by the image sensor 108 of the base computing device 104. In the example of FIG. 5, the lamp 188, table 122 and doorway 144 may be rendered images assembled from the 3D model 322 of the room 100.

With image data 318 displayed on the smart phone 120, the user 102 may provide user input 326 that comprises position data 330 of an object 338 of interest and includes a semantic identifier 334 for the object. Such user input may be received by the base computing device 104 and processed to associate the semantic identifier 334 with the object 338, as described in more detail below. In some examples, the display 303 of the smart phone 120 may comprise a touch-screen display. In these examples, the user 102 may provide position data 330 of an object 338 of interest by touching the image of the object displayed on the touch-sensitive display 303. Position data 330 may then be derived from the touch selection of the object image. For example and with reference to FIG. 5, where the user desires to provide a semantic identifier for the lamp 118, the user 102 may touch the display 303 at touchpoint 408 that overlaps the displayed image of the lamp.

The touchpoint 408 may be detected by smart phone 120 at a two-dimensional (x, y) location on the display 303, and translated to a two-dimensional location in the corresponding image data. This position data may be sent to the base computing device 104. With reference also to FIG. 4, the base computing device 104 may then map the position data to a 3D location 342 in the 3D model 322 at which the lamp 118 is located.

In some examples, spatial transformation of the touch selection 408 to a 3D location 342 in the 3D model 322 may be accomplished using the known 3D position of the image sensor 108 in base computing device 104. For example, the touch selection 408 on display 303 may be translated to an (x, y) pixel location in the image data 318 displayed on the display. In some examples, this (x, y) pixel location may be transformed into a frame of reference of the base computing device 104. For example, the base computing device 104 may establish a coordinate system in which the image sensor 108 is the origin, and the (x, y) pixel location may be mapped to this coordinate system.

In some examples, the (x, y) pixel location initially may be converted to a 3D ray extending in the z-direction from the point of the touch selection 408 through the position of the lamp 118 to infinity. Using depth information of the lamp 118 in the 3D model 322 of the room 100, the z-coordinate corresponding to the collision of the 3D ray with the 3D position of the lamp 118 may be determined. As noted above, depth information of the lamp 118 may be determined using any suitable technique. The 3D location 342 of the lamp 118 may be recorded and stored by base computing device 104. As the 3D model 322 of the room 100 may be based on a frame of reference of the base computing device 104, the 3D location 342 of lamp 118 may be stored in the same frame of reference.

In some examples, a position anchor may be fixed in space at the position occupied by the lamp 118 along the 3D ray extending from the touch selection 408. For example, a position anchor may be fixed at the location where the 3D ray intersects a surface mesh of the lamp 118, thereby indicating the depth of the lamp.

In other examples, other spatial mapping techniques may be used to map the position data of the touch selection 408 to a 3D location 342 in the 3D model 322 at which the lamp 118 is located. For example, a pixel mapping technique may identify one or more pixels of the image data that are selected by the touch selection 408 and correspond to the lamp 118. By analyzing the image data 318 captured by its image sensor 108, the base computing device 104 may determine which pixel(s) in the image data 318 match the identified pixels selected by the touch selection 408. The base computing device 104 may then map the location of these pixel(s) to the 3D location 342 of the lamp 118 in 3D model 322.

In addition to touching the display 303 to provide position data of the lamp 118, the user 102 also provides a semantic identifier 334 for the lamp. For example and as noted above, the user may provide user input 326 including a semantic identifier 334 in the form of voice input. The semantic identifier 334 may be derived from the voice input as described above. In some examples, base computing device 104 may associate the semantic identifier 334 with the lamp 118 when the voice input is provided contemporaneously with touch selection 408 identifying the lamp. For example, the semantic identifier 334 may be associated with the lamp 118 when the touch selection 408 and semantic identifier are provided simultaneously or within a temporally overlapping timeframe. In other examples, the semantic identifier 334 may be associated with the lamp 118 when the touch selection 408 and semantic identifier are both provided within a predetermined timeframe, such as 1 second, 2 seconds, or other suitable timeframe.

In the example of FIGS. 1 and 5, the user 102 may say "this is the living room lamp" while touching the screen 303 at touch selection 408. The base computing device 104 may derive the semantic identifier "living room lamp" from the voice input. Based on receiving the semantic identifier "living room lamp" and mapping the touch selection 408 to the 3D location of the lamp 118, the base computing device 104 may associate the semantic identifier "living room lamp" with the lamp 118. In other examples, the user 102 may provide a semantic identifier 334 via other forms of user input, such as text or sign language.

In other examples, the user 102 may provide position data 330 of a desired object 338 by touching the object or gesturing to indicate the object. In these examples, the position data 330 may comprise image data 318 from the image sensor 108 of the base computing device 104, with the image data indicating a user physically touching or gesturing to indicate the object 338.

For example, the user 102 may walk over and touch the lamp 118 with her finger while saying "this is the living room lamp" to semantically label the lamp 118 as the "living room lamp." The base computing device 104 may capture image data 318 showing the user 102 touching the lamp 118. As long as the user 102 is within the field of view 140 of the base computing device 104, the base computing device may track the spatial location of the user 102 and identify the user's finger physically touching the lamp 118. By also receiving the semantic identifier "living room lamp" when the user 102 touches the lamp 118, the base computing device 104 may associate the semantic identifier "living room lamp" with the lamp 118. Additionally, and by providing the image data 318 from the image sensor 108 to the smart phone 102, the base computing device 104 may enable the user 102 to confirm that the user and lamp 118 are within the field of view 140 of the base computing device.

In some examples, mapping the position data 330 to a 3D location 342 in the 3D model 322 may comprise performing object recognition to determine that the object 338 is a known object 350. In some examples, instructions 304 of base computing device 300 may comprise an image classifier application that may process the image data 318 and the position data 330 to identify the object 338 as a known object 338. In one example, an object recognition system comprising an image classifier may infer a mesh on top of a recognized object. The image classifier may comprise a neural network trained on object recognition and classification. For example and with reference to FIGS. 1 and 5, lamp 118 may be identified as a lamp by an image classifier.

In some examples, an object 338 may comprise a smart object that may be capable of communicatively coupling to base computing device 300 to enable the device to control the smart object. In the example of FIG. 1, the television 112, speakers 114, motorized curtains 116, and/or lamp 118 may be smart objects. In some examples, initially the base computing device 300 may not be communicatively coupled to a smart object 338. In these examples, after mapping the position data 330 to the 3D location 322 of the smart object 338 and associating the semantic identifier 334 with the object, the base computing device 300 may establish a communicative coupling with the object.

In some examples, based on mapping the position data 330 and associating the semantic identifier 334 with a smart object, the base computing device 300 may ask the user if she would like the device to connect to the smart object. For example, in FIG. 1 the base computing device 104 may broadcast a query to the user 102, "Would you like me to learn how to connect to the living room lamp?" Upon receiving affirmative user input, the base computing device 104 the may start a binding process to communicatively couple to the lamp 118.

Once an object 338 is semantically labeled, its visual model and 3D location 342 may be stored in base computing device 300. If the base computing device 300 is moved to an updated location or orientation, the base computing device may determine that it has been moved and/or reoriented via changes in the image data 318 or other sensor inputs. Accordingly, the base computing device 300 may perform corresponding transformations to update the 3D model 322 of its surrounding environment and the 3D location(s) of object(s) 338 in the environment relative to its updated location/orientation. Such transformations may be performed using, for example, simultaneous localization and mapping (SLAM) or other suitable techniques. In a similar manner, the base computing device 300 may determine that an object 338 is moved to an updated location, and may correspondingly update the object's stored 3D location 342 in the 3D model 322 to reflect its updated location.

In some examples, changes in the environment may result in an object 338 being fully or partially blocked from view or out of view of the image sensor(s) 312 of the base computing device 300. For example, an object 338 of interest may be moved out of the field of view of the base computing device 300, or another object may be placed between the object of interest and the image sensor(s) 312 of the base computing device. In these examples, upon analyzing changes in the image data 318 to determine that an object 338 is blocked from view or out of view, the base computing device 300 may notify a user that it can no longer view the object. For example, if lamp 118 is moved outside of the field of view 140 of the base computing device 104, the base computing device may provide audio output that communicates, "I can no longer see the living room lamp."

As noted above, in some examples one or more aspects of the methods and processes for associating a semantic identifier with an object described herein may be performed via other computing devices. FIG. 6 shows an example implementation in which one or more remote services 170 perform one or more aspects of the methods and processes for associating a semantic identifier with an object, as well as the natural language processing functionality of intelligent assistant system 20. In this example, instructions 304, voice listener 30, parser 40, intent handler 50, entity tracker 10 and commitment engine 60 reside on one or more computing devices, such as one or more servers, that are remotely located from a cloud-supported base computing device A. Sensor data from one or more sensors 22 of the base computing device A is provided to remote service(s) 170 via a network. For example, audio data of a user speaking may be captured by a microphone of base computing device A and provided to voice listener 30.

As described above, voice listener 30, parser 40, and intent handler 50 cooperate to convert the audio data into commitments that are stored in commitment engine 60. At a contextually appropriate time, the commitment engine 60 may execute a commitment and provide output, such as audio signals, to one or more output device(s) 70 of the base computing device A.

FIG. 7 shows another example implementation in which one or more remote services 170 perform one or more aspects of the methods and processes for associating a semantic identifier with an object and processing natural language inputs. In this example, the one or more remote services 170 are communicatively coupled with a plurality of different sensors 22 and output devices 70. In this example, the sensors include individual standalone sensors A and C, such as microphones, cameras, etc. The output devices include individual standalone output devices B and D, such as loudspeakers.

The one or more remote services 170 are also communicatively coupled to a base computing device B that includes one or more sensors F and an output device G. Base computing device B may take the form of a simple standalone device comprising a camera, microphone, speaker and network connectivity components. In some examples, device B, sensors A and C, and output devices B and D may be part of the same cloud-supported client. In other examples, any number of individual sensors and devices may be utilized with the one or more remote services 170.

As described above, the one or more remote services 170 perform one or more aspects of associating a semantic identifier with an object, as well as aspects of the natural language processing functionality of intelligent assistant system 20. In some examples, and using image data from a base computing device, one or more of the remote services 170 may perform all aspects of the methods and processes for associating a semantic identifier with an object. In other examples, one or more remote services 170 may perform less than all aspects of the methods and processes for associating a semantic identifier with an object, and may be communicatively coupled to the other computing devices located at one or more other service(s).

Figure 8:
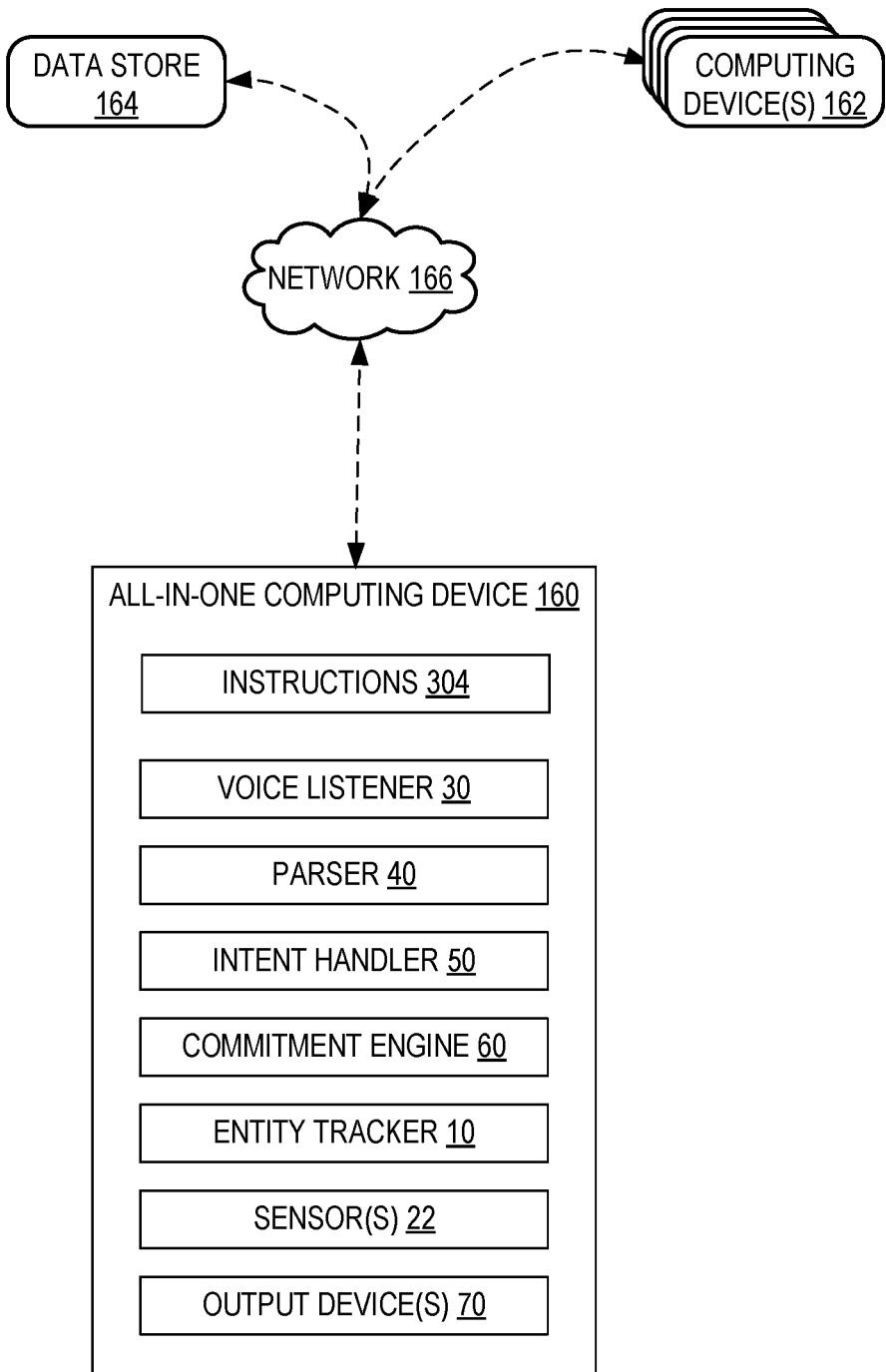
FIG. 8 schematically shows an all-in-one computing device that implements aspects of associating a semantic identifier with an object according to examples of the present disclosure.

FIG. 8 shows an example embodiment of a base computing device in the form of an all-in-one computing device 160 in which the instructions 304 and components implementing intelligent assistant system 20 are stored and arranged together in a standalone device. In some examples, all-in-one computing device 160 may be communicatively coupled to one or more other computing devices 162 via a network 166. In some examples, all-in-one computing device 160 may be communicatively coupled to a data store 164 that may store a variety of data, such as user profile data. All-in-one computing device 160 includes instructions 304, at least one sensor 22, voice listener 30, parser 40, intent handler 50, commitment engine 60, entity tracker 10, and at least one output device 70. Sensor(s) 22 include at least one image sensor and microphone to receive image data and natural language inputs from a user. In some examples one or more other types of sensor(s) 22 also may be included.

Figure 9:
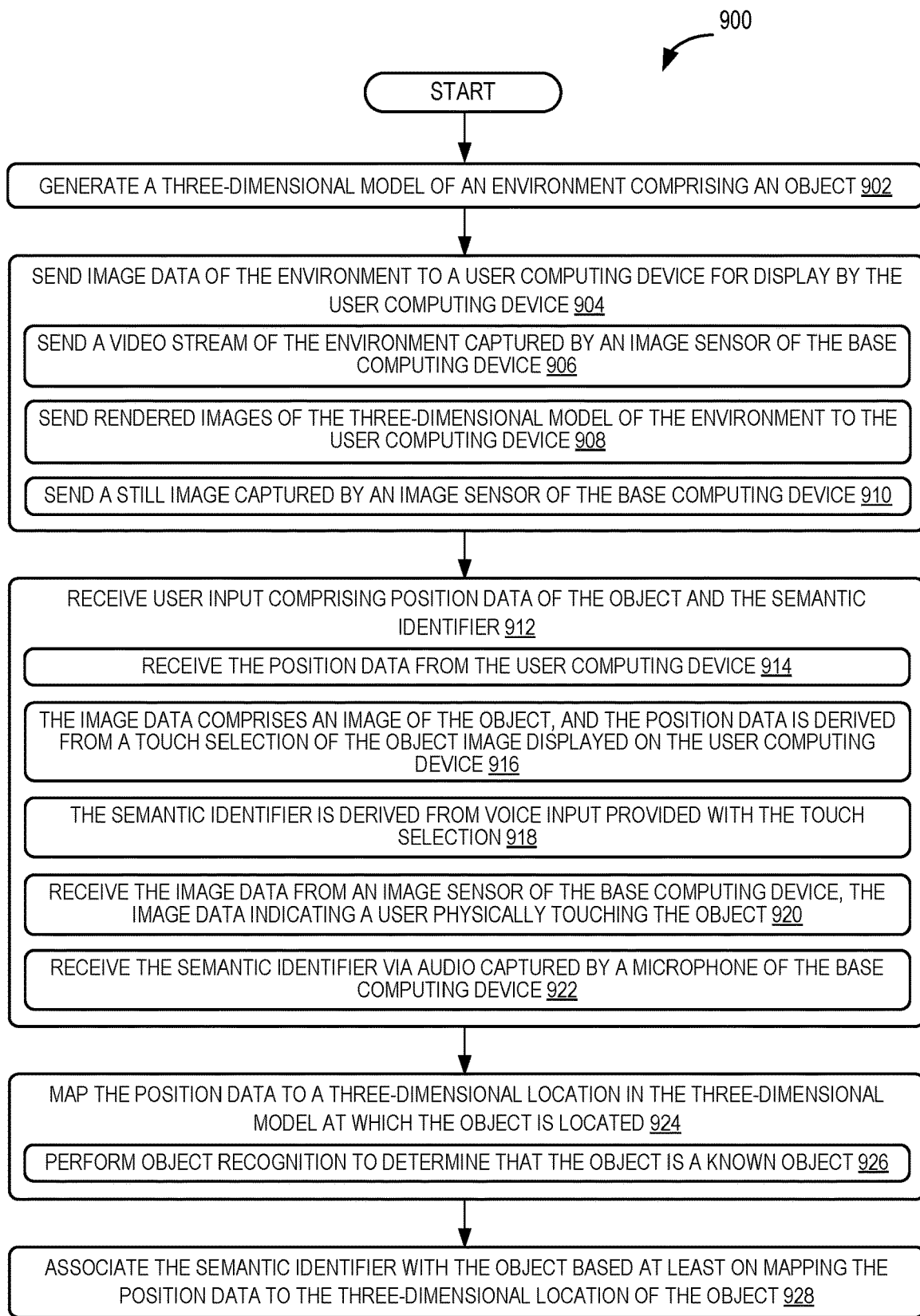
FIG. 9 is a block diagram of a method for associating a semantic identifier with an object according to examples of the present disclosure.

FIG. 9 illustrates an example method 900 for associating a semantic identifier with an object that at least partially addresses the problems described above. The following description of method 900 is provided with reference to the software and hardware components described above and shown in FIGS. 1-8. Method 900 may be performed by base computing devices 104 and 300, one or more remote computing devices comprising remote service(s) 170 of FIG. 7, and/or all-in-one computing device 160 of FIG. 8, as examples. An "environment" as used herein may refer to any real-world area, such as a single room, house, apartment, store, office, building, venue, outdoor space, grid sector, etc. It will also be appreciated that method 900 also may be performed in other contexts using other suitable hardware and software components.

With reference to FIG. 9, at 902 the method 900 may include generating a 3D model of an environment comprising an object. At 904, the method 900 may include sending image data of the environment to a user computing device for display by the user computing device. At 906, the method 900 may include sending a video stream of the environment captured by an image sensor of the base computing device. At 908 the method 900 may include sending rendered images of the 3D model of the environment to the user computing device. At 910, the method 900 may include sending a still image captured by a camera of the base computing device.

At 912, the method 900 may include receiving user input comprising position data of the object and the semantic identifier. At 914, the method 900 may include receiving the position data from the user computing device. At 916, the method 900 may include wherein the image data comprises an image of the object, and the position data is derived from a touch selection of the object image displayed on the user computing device. At 918, the method 900 may include wherein the semantic identifier is derived from voice input provided with the touch selection. At 920, the method 900 may include receiving the image data from an image sensor of the base computing device, the image data indicating a user physically touching the object. At 922, the method 900 may include receiving the semantic identifier via audio captured by a microphone of the base computing device.

At 924, the method 900 may include mapping the position data to a 3D location in the 3D model at which the object is located. At 926, the method 900 may include performing object recognition to determine that the object is a known object. At 928, the method 900 may include associating the semantic identifier with the object based at least on mapping the position data to the 3D location of the object.

It will be appreciated that method 900 is provided by way of example and is not meant to be limiting. Therefore, it is to be understood that method 900 may include additional and/or alternative steps relative to those illustrated in FIG. 9. Further, it is to be understood that method 900 may be performed in any suitable order. Further still, it is to be understood that one or more steps may be omitted from method 900 without departing from the scope of this disclosure.

In some embodiments, the methods and processes described herein may be tied to a computing system of one or more computing devices. In particular, such methods and processes may be implemented as a computer-application program or service, an application-programming interface (API), a library, and/or other computer-program product.

Figure 10:
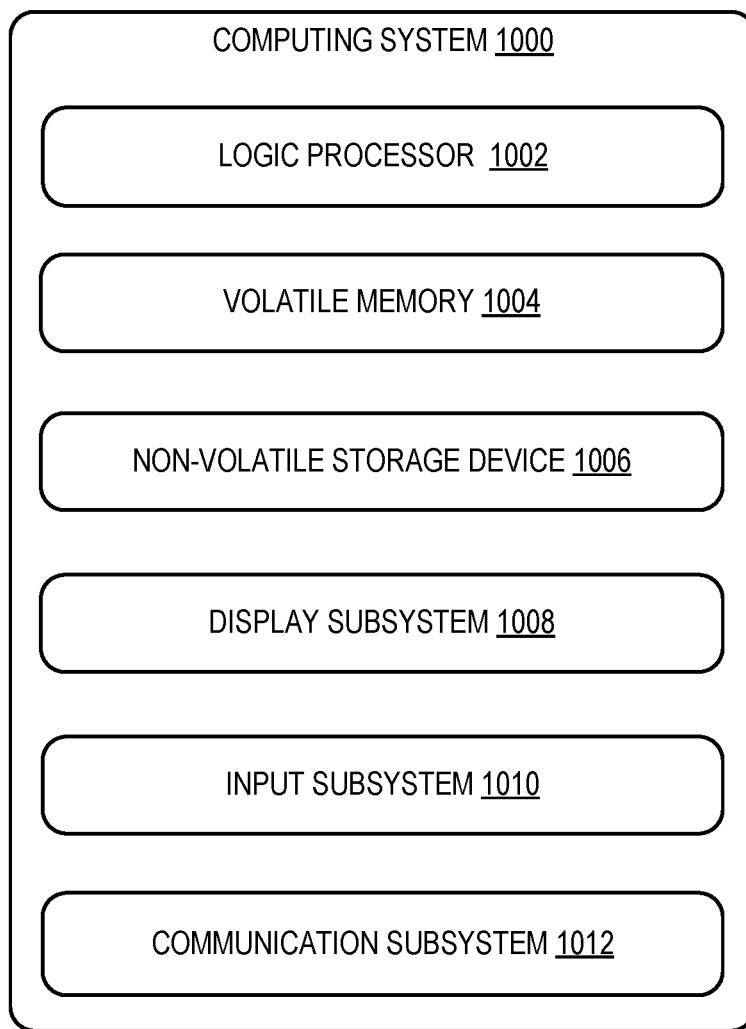
FIG. 10 shows a block diagram of an example computing device according to examples of the present disclosure.

FIG. 10 schematically shows a non-limiting embodiment of a computing system 1000 that can enact one or more of the methods and processes described above. Computing system 1000 is shown in simplified form. Computing system 1000 may take the form of one or more smart assistant devices, personal computers, server computers, tablet computers, home-entertainment computers, network computing devices, gaming devices, mobile computing devices, mobile communication devices (e.g., smart phone), and/or other computing devices Computing system 1000 includes a logic processor 1002, volatile memory 1004 and a non-volatile storage device 1006. Computing system 1000 may optionally include a display subsystem 1008, input subsystem 1010, communication subsystem 1012, and/or other components not shown in FIG. 10.

Logic processor 1002 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1002 may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration. In such a case, these virtualized aspects are run on different physical logic processors of various different machines, it will be understood.

Non-volatile storage device 1006 includes one or more physical devices configured to hold instructions executable by the logic processors to implement the methods and processes described herein. When such methods and processes are implemented, the state of non-volatile storage device 1006 may be transformed—e.g., to hold different data.

Non-volatile storage device 1006 may include physical devices that are removable and/or built-in. Non-volatile storage device 1006 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Non-volatile storage device 1006 may include nonvolatile, dynamic, static, read/write, read-only, random-access, sequential-access, location-addressable, file-addressable, and/or content-addressable devices. It will be appreciated that non-volatile storage device 1006 is configured to hold instructions even when the power is cut to the non-volatile storage device 1006.

Volatile memory 1004 may include physical devices that include random access memory. Volatile memory 1004 is typically utilized by logic processor 1002 to temporarily store information during processing of software instructions. It will be appreciated that volatile memory 1004 typically does not continue to store instructions when power is cut to the volatile memory 1004, Aspects of logic processor 1002 and non-volatile storage device 1006 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "program," "module," "engine" and "application" may be used to describe an aspect of computing system 1000 implemented in software by a processor to perform a particular function using portions of volatile memory, which function involves transformative processing that specifically configures the processor to perform the function. Thus, a program, module, engine or application may be instantiated via logic processor 1002 executing instructions held by non-volatile storage device 1006, using portions of volatile memory 1004. It will be understood that different programs, modules, engines and/or applications may be instantiated from the same application, service, code block, object, library, routine, API, function, etc. Likewise, the same module, program, engine and/or application may be instantiated by different applications, services, code blocks, objects, routines, APIs, functions, etc. The terms "program," "module," "engine" and "application" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 1008 may be used to present a visual representation of data held by non-volatile storage device 1006. This visual representation may take the form of a graphical user interface (GUI). As the herein described methods and processes change the data held by the storage machine, and thus transform the state of the storage machine, the state of display subsystem 1008 may likewise be transformed to visually represent changes in the underlying data. Display subsystem 1008 may include one or more display devices utilizing virtually any type of technology. Such display devices may be combined with logic processor 1002, volatile memory 1004 and/or non-volatile storage device 1006 in a shared enclosure, or such display devices may be peripheral display devices.

When included, input subsystem 1010 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1012 may be configured to communicatively couple computing system 1000 with one or more other computing devices. Communication subsystem 1012 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1000 to send and/or receive messages to and/or from other devices via a network such as the Internet.

The following paragraphs provide additional support for the claims of the subject application. One aspect provides a base computing device communicatively coupled to a user computing device, the base computing device comprising: a logic processor, and a storage device holding instructions executable by the logic processor to generate a three-dimensional model of an environment comprising an object, send image data of the environment to the user computing device for display by the user computing device, receive user input comprising position data of the object and a semantic identifier, map the position data to a three-dimensional location in the three-dimensional model at which the object is located, and based at least on mapping the position data to the three-dimensional location of the object, associate the semantic identifier with the object.

The base computing device may additionally or alternatively include, wherein receiving user input comprises receiving the position data from the user computing device. The base computing device may additionally or alternatively include, wherein the image data comprises an image of the object, and the position data is derived from a touch selection of the object image displayed on the user computing device. The base computing device may additionally or alternatively include, wherein the semantic identifier is derived from voice input provided with the touch selection.

The base computing device may additionally or alternatively include, wherein receiving user input comprises receiving the image data from an image sensor of the base computing device, the image data indicating a user physically touching the object. The base computing device may additionally or alternatively include, wherein receiving user input comprises receiving the semantic identifier via audio captured by a microphone of the base computing device.

The base computing device may additionally or alternatively include, wherein sending the image data of the environment to the user computing device comprises sending a video stream of the environment captured by an image sensor of the base computing device. The base computing device may additionally or alternatively include, wherein sending the image data of the environment to the user computing device comprises sending rendered images of the three-dimensional model of the environment to the user computing device. The base computing device may additionally or alternatively include, wherein sending the image data of the environment to the user computing device comprises sending a still image captured by an image sensor of the base computing device. The base computing device may additionally or alternatively include, wherein mapping the position data to a three-dimensional location in the three-dimensional model further comprises performing object recognition to determine that the object is a known object.

Another aspect provides at a base computing device, a method for associating a semantic identifier with an object, the method comprising: generating a three-dimensional model of an environment comprising the object, sending image data of the environment to a user computing device for display by the user computing device, receiving user input comprising position data of the object and the semantic identifier, mapping the position data to a three-dimensional location in the three-dimensional model at which the object is located, and based at least on mapping the position data to the three-dimensional location of the object, associating the semantic identifier with the object.

The method may additionally or alternatively include, wherein receiving user input comprises receiving the position data from the user computing device. The method may additionally or alternatively include wherein the image data comprises an image of the object, and the position data is derived from a touch selection of the object image displayed on the user computing device. The method may additionally or alternatively include wherein the semantic identifier is derived from voice input provided with the touch selection.

The method may additionally or alternatively include wherein receiving user input comprises receiving the image data from an image sensor of the base computing device, the image data indicating a user physically touching the object. The method may additionally or alternatively include wherein receiving user input comprises receiving the semantic identifier via audio captured by a microphone of the base computing device.

The method may additionally or alternatively include wherein sending the image data of the environment to the user computing device comprises sending a video stream of the environment captured by an image sensor of the base computing device. The method may additionally or alternatively include wherein sending the image data of the environment to the user computing device comprises sending rendered images of the three-dimensional model of the environment to the user computing device. The method may additionally or alternatively include wherein mapping the position data to a three-dimensional location in the three-dimensional model further comprises performing object recognition to determine that the object is a known object.

Another aspect provides, at a base computing device communicatively coupled to a user computing device, a method comprising: generating a three-dimensional model of an environment comprising an object, sending image data of the environment to the user computing device for display by the user computing device, receiving user input comprising position data and a semantic identifier, wherein the position data corresponds to a touch selection on the user computing device, mapping the position data to a three-dimensional location in the three-dimensional model at which the object is located, and based at least on mapping the position data to the three-dimensional location of object, associating the semantic identifier with the object.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A base computing device communicatively coupled to a user computing device, the base computing device comprising:
    a logic processor; and
    a storage device holding instructions executable by the logic processor to:
        generate a three-dimensional model of a physical environment, wherein the physical environment comprises a physical object that is not associated with a semantic identifier;
        send image data of the physical environment to the user computing device for display by the user computing device, wherein the image data comprises an object image of the physical object;
        receive from the user computing device user input comprising (1) position data of the physical object, wherein the position data is derived from a touch selection of the object image displayed on the user computing device, and (2) an initial semantic identifier, wherein the initial semantic identifier was not previously associated with the physical object;
        map the position data to a three-dimensional location in the three-dimensional model at which the physical object is located; and
        based at least on mapping the position data to the three-dimensional location of the physical object, associate the initial semantic identifier with the physical object.

2. The base computing device of claim 1, wherein the initial semantic identifier is derived from voice input provided with the touch selection.

3. The base computing device of claim 1, wherein receiving user input comprises receiving the image data from an image sensor of the base computing device, the image data indicating a user physically touching the physical object.

4. The base computing device of claim 1, wherein receiving user input comprises receiving the initial semantic identifier via audio captured by a microphone of the base computing device.

5. The base computing device of claim 1, wherein sending the image data of the physical environment to the user computing device comprises sending a video stream of the physical environment captured by an image sensor of the base computing device.

6. The base computing device of claim 1, wherein sending the image data of the physical environment to the user computing device comprises sending rendered images of the three-dimensional model of the physical environment to the user computing device.

7. The base computing device of claim 1, wherein sending the image data of the physical environment to the user computing device comprises sending a still image captured by an image sensor of the base computing device.

8. The base computing device of claim 1, wherein mapping the position data to a three-dimensional location in the three-dimensional model further comprises performing object recognition to determine that the physical object is a known object.

9. At a base computing device, a method for associating an initial semantic identifier with a physical object, the method comprising:
    generating a three-dimensional model of a physical environment, wherein the physical environment comprises the physical object, and wherein the physical object is not associated with a semantic identifier;
    sending image data of the physical environment to a user computing device for display by the user computing device, wherein the image data comprises an object image of the physical object;

receiving from the user computing device user input comprising (1) position data of the physical object, wherein the position data is derived from a touch selection of the object image displayed on the user computing device, and (2) the initial semantic identifier, wherein the initial semantic identifier was not previously associated with the physical object;

mapping the position data to a three-dimensional location in the three-dimensional model at which the physical object is located; and based at least on mapping the position data to the three-dimensional location of the physical object, associating the initial semantic identifier with the physical object.

10. The method of claim 9, wherein the initial semantic identifier is derived from voice input provided with the touch selection.

11. The method of claim 9, wherein receiving user input comprises receiving the image data from an image sensor of the base computing device, the image data indicating a user physically touching the physical object.

12. The method of claim 9, wherein receiving user input comprises receiving the initial semantic identifier via audio captured by a microphone of the base computing device.

13. The method of claim 9, wherein sending the image data of the physical environment to the user computing device comprises sending a video stream of the physical environment captured by an image sensor of the base computing device.

14. The method of claim 9, wherein sending the image data of the physical environment to the user computing device comprises sending rendered images of the three-dimensional model of the physical environment to the user computing device.

15. The method of claim 9, wherein mapping the position data to a three-dimensional location in the three-dimensional model further comprises performing object recognition to determine that the physical object is a known object.

16. At a base computing device communicatively coupled to a user computing device, a method comprising:

generating a three-dimensional model of a physical environment, wherein the physical environment comprises a physical object that is not associated with a semantic identifier;

sending image data of the physical environment to the user computing device for display by the user computing device, wherein the image data comprises an object image of the physical object;

receiving from the user computing device user input comprising (1) position data and (2) an initial semantic identifier, wherein the position data corresponds to a touch selection on the user computing device, and wherein the initial semantic identifier was not previously associated with the physical object;

mapping the position data to a three-dimensional location in the three-dimensional model at which the physical object is located; and based at least on mapping the position data to the three-dimensional location of the physical object, associating the initial semantic identifier with the physical object.

* * * * *